(12) United States Patent
Nervo et al.

(10) Patent No.: US 11,919,015 B2
(45) Date of Patent: Mar. 5, 2024

(54) GAS-FILLED RESILIENT BODY AND USE THEREOF

(71) Applicant: DISPENSING TECHNOLOGIES B.V., Eindhoven (NL)

(72) Inventors: Paulo Nervo, Hoogeloon (NL); Dennis Van Melick, Eindhoven (NL); Dominicus Jan Van Wijk, Helmond (NL)

(73) Assignee: DISPENSING TECHNOLOGIES B.V., Eindhoven (NL)

( * ) Notice: Subject to any disclaimer, the term of this patent is extended or adjusted under 35 U.S.C. 154(b) by 154 days.

(21) Appl. No.: 17/297,089

(22) PCT Filed: Nov. 26, 2019

(86) PCT No.: PCT/EP2019/082641
§ 371 (c)(1),
(2) Date: May 26, 2021

(87) PCT Pub. No.: WO2020/109340
PCT Pub. Date: Jun. 4, 2020

(65) Prior Publication Data
US 2022/0025981 A1    Jan. 27, 2022

(30) Foreign Application Priority Data
Nov. 26, 2018 (NL) .................................. 2022072

(51) Int. Cl.
*B05B 11/00* (2023.01)
*B05B 1/30* (2006.01)
(Continued)

(52) U.S. Cl.
CPC ........ *B05B 11/0054* (2013.01); *B05B 1/3006* (2013.01); *B05B 9/0833* (2013.01); *B05B 11/007* (2013.01); *B05B 11/0081* (2013.01); *B05B 11/047* (2013.01); *B05B 11/104* (2023.01); *B05B 11/1077* (2023.01); *B65D 81/3222* (2013.01); *F16K 15/141* (2013.01); *F16K 15/142* (2013.01); *F16K 21/00* (2013.01);
(Continued)

(58) Field of Classification Search
CPC .............. B05B 11/0054; B05B 11/007; B05B 11/0081; B05B 11/001; B05B 11/109; B05B 11/1077; B05B 11/1011; B05B 11/047; B05B 1/3006; B05B 9/0833; B65D 81/3222; F16K 15/142; F16K 15/141; F16K 15/1825; A61M 5/2053; G01F 11/08
USPC ........ 222/92–107, 1, 632, 633, 394; 604/70, 604/212–214, 140–147
See application file for complete search history.

(56) References Cited

U.S. PATENT DOCUMENTS 3,089,489 A * 5/1963 Dunmire ............... A61M 5/282
                                                              604/212
3,319,837 A    5/1967 Mueller
(Continued)

OTHER PUBLICATIONS

International Search Report and Written Opinion for the International Patent Application No. PCT/EP2019/082641, dated Feb. 20, 2020, 12 pages.

*Primary Examiner* — Lien M Ngo
(74) *Attorney, Agent, or Firm* — KDW Firm PLLC

(57) ABSTRACT

A gas-filled resilient body and uses thereof are described. The gas-filled resilient body may be used as a valve member, as a spring or as a gas-propelled dispenser.

20 Claims, 23 Drawing Sheets

(51) Int. Cl.
    *B05B 9/08*     (2006.01)
    *B05B 11/04*     (2006.01)
    *B05B 11/10*     (2023.01)
    *B65D 81/32*     (2006.01)
    *F16K 15/14*     (2006.01)
    *F16K 21/00*     (2006.01)
    *G01F 11/08*     (2006.01)
    *A61M 5/20*     (2006.01)
    *F16K 15/18*     (2006.01)

(52) U.S. Cl.
    CPC ..... *G01F 11/08* (2013.01); *A61M 2005/2013* (2013.01); *A61M 5/2053* (2013.01); *B05B 11/001* (2013.01); *B05B 11/1011* (2023.01); *F16K 15/1825* (2021.08)

(56) References Cited

U.S. PATENT DOCUMENTS

| | | | |
|---|---|---|---|
| 3,498,321 A | | 3/1970 | Barrett |
| 3,560,267 A | | 2/1971 | Guilliams |
| 3,970,106 A | | 7/1976 | Harris |
| 4,651,905 A | * | 3/1987 | Hayes ................. B65D 83/207 222/394 |
| 5,641,004 A | * | 6/1997 | Py ........................... B65B 55/02 141/10 |
| 2011/0262550 A1 | * | 10/2011 | Klofta .................... A61P 17/00 514/390 |
| 2013/0197475 A1 | * | 8/2013 | Dunn ................. A61M 5/2033 604/199 |
| 2014/0008366 A1 | | 1/2014 | Genosar |

* cited by examiner

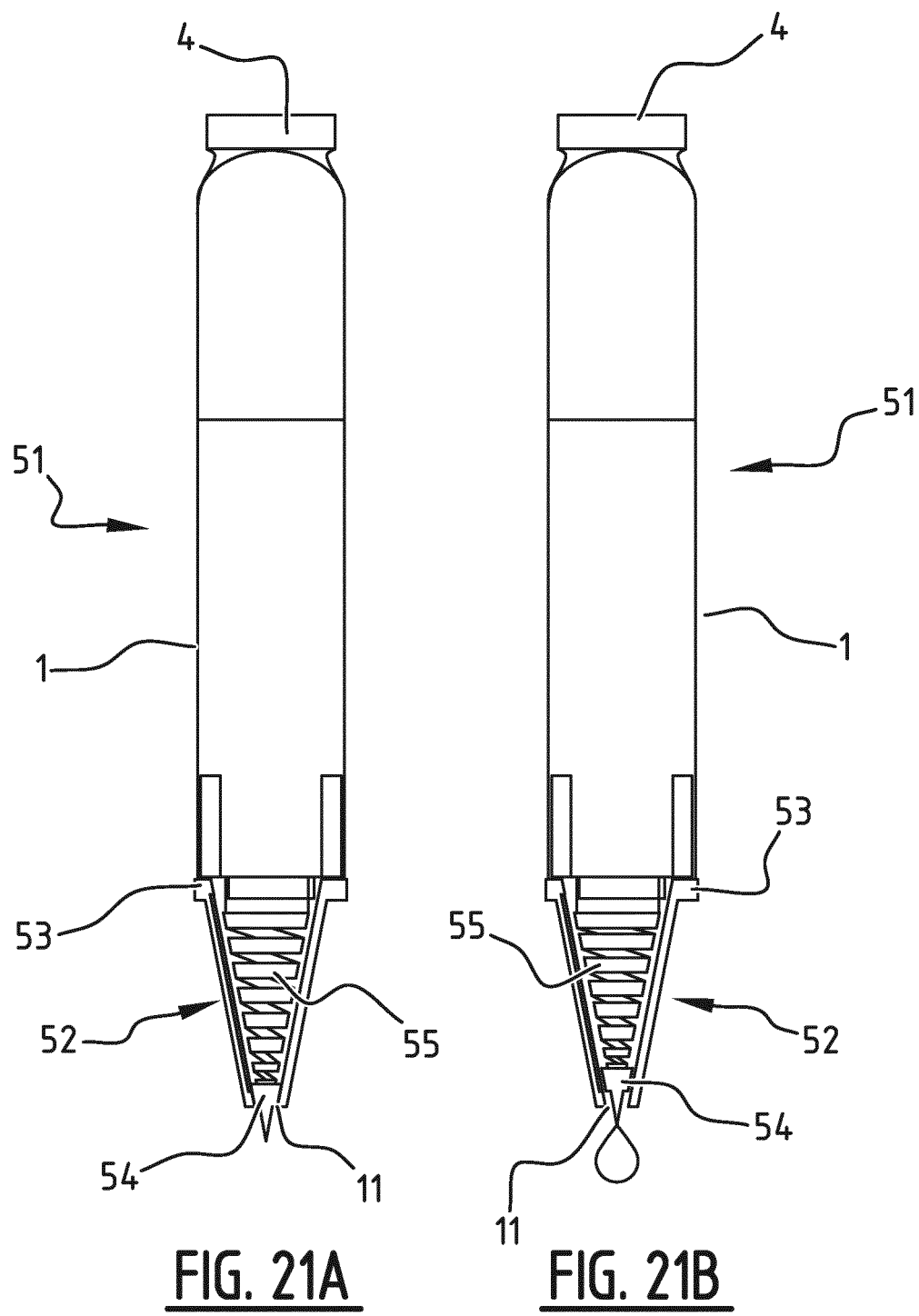

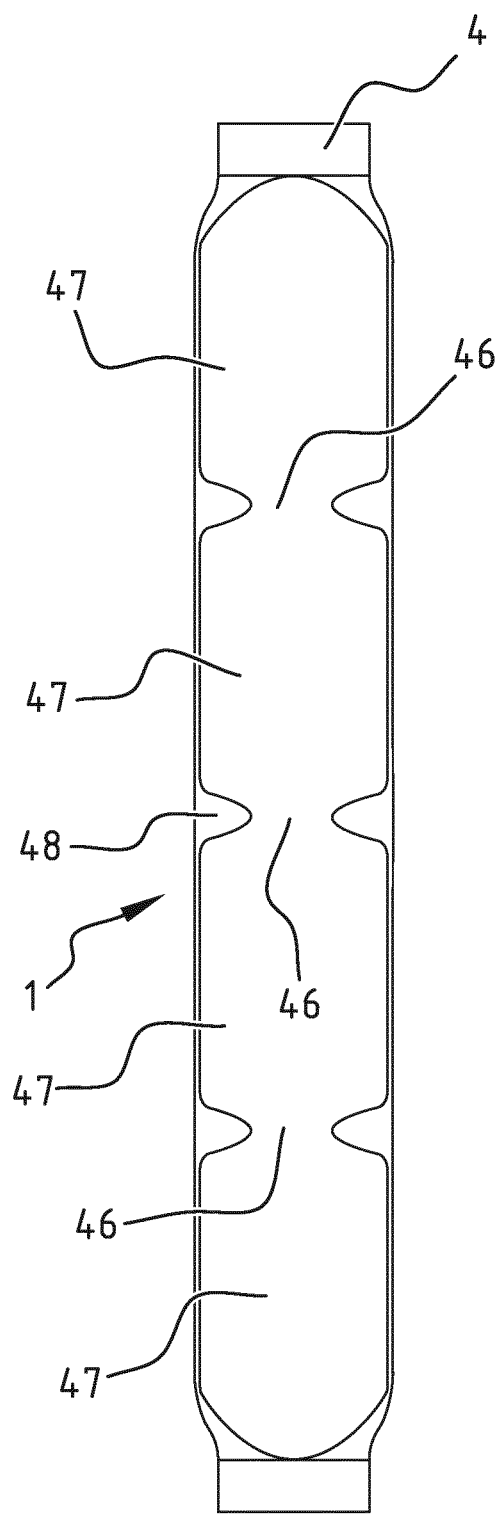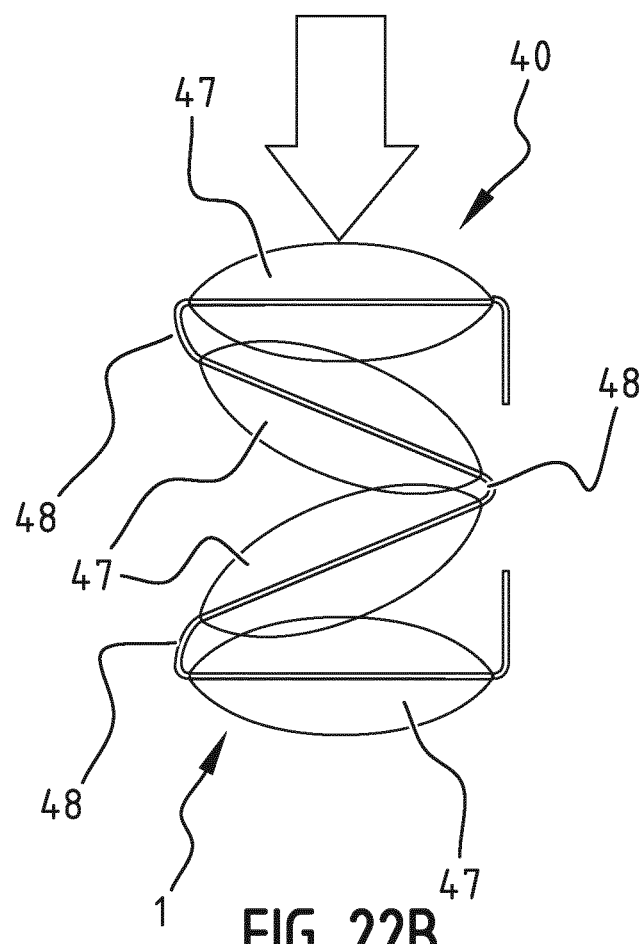
FIG. 22A
FIG. 22B

GAS-FILLED RESILIENT BODY AND USE THEREOF

This is a national stage application filed under 35 U.S.C. § 371 of international application PCT/EP2019/082641, filed Nov. 26, 2019, which claims priority to Netherlands Patent Application No. 2022072, filed Nov. 26, 2018, the entirety of which applications are hereby incorporated by reference herein.

The invention relates to a resilient hollow body that is at least partially filled with a compressed gas to establish an internal gas pressure within the hollow body. In particular, the invention relates to various ways of using such a resilient gas-filled body.

A resilient gas-filled body for use in the invention can be a single layer or multi-layer extruded tube of which the ends have been closed after the tube has been filled with gas. Alternatively, the resilient body can be made of a single layer of foil or a foil laminate. The resilient body can also be made by injection molding or blow molding.

In accordance with a first aspect of the invention, a gas-filled resilient body is used as a valve member. As a result of the resilience of the body, supported by the pressure of the gas with which it is filled, such a valve member will always return to its initial state when it is not loaded. In this way the valve member may be used without the need for any separate return mechanism. Moreover, the gas-filled resilient body can be made of plastics that can be easily recycled, like e.g. PE or PP. Conventional valves, on the other hand, are often made of more exotic plastics like POM or even of metal. This causes problems in recycling.

In one embodiment, the gas-filled resilient body may be part of a normally closed valve which opens upon deformation of the gas-filled resilient body. Such a normally closed valve is particularly useful for e.g. material dispensers.

In a further development, the gas-filled resilient body may be fittingly arranged in a valve housing and deformation of the gas-filled resilient body may unblock a flow path between an inflow opening and an outflow opening of the valve housing. The gas-filled resilient body may e.g. be lifted from a valve seat or be urged away from a wall of the valve housing to allow fluid flow between the inflow and outflow openings.

In one embodiment, the gas-filled resilient body may be deformed by an increase in pressure of a fluid to be dispensed through the valve. This pressure rise may be due to conscious pressurization of the fluid, e.g. in a dispensing operation, or it may be unwanted, in which case the valve acts as an overpressure valve.

In another embodiment, the gas-filled resilient body may be mechanically deformed by an operating member. For instance, a user may operate a button or lever to open the valve.

In accordance with a second aspect of the invention, a gas-filled resilient body is used as a spring. As stated above, the resilient body, supported by the pressure of the gas with which it is filled, will always try to return to its initial state, which makes is ideally suited to act as a spring.

In one embodiment of the spring, the gas-filled resilient body may be configured to have a predetermined spring characteristic. For instance, the body may have a cross-sectional area which varies in the direction of an expected load, so that a conical spring is formed.

In a further embodiment, a plurality of gas-filled bodies may be combined to provide the predetermined spring characteristic. For instance, a number of more or less identical bodies may be stacked to form a spring which has a higher spring constant than an individual gas-filled resilient body.

Alternatively or additionally, the gas-filled resilient body may include a plurality of chambers which may be combined to provide the predetermined spring characteristic. For instance a body having a series of more or less identical chambers may be folded to form a stack of chambers.

In accordance with a third aspect, the invention relates to the use of a partially gas-filled resilient body as a gas-propelled dispenser, wherein the resilient body is filled with gas and a material to be dispensed. In this way a structurally simple dispenser is obtained, which may be manufactured at low cost. Moreover, such a dispenser does not require venting when the material is dispensed, and the propellant gas ensures a homogenous distribution of the material to be dispensed.

In one embodiment, the material to be dispensed may be a liquid or a particulate material. Such materials can easily be expelled from the resilient body by the pressurized gas in the body.

In a further embodiment, the material may be dispensed by piercing the resilient body. In this way the dispenser does not require any valve and is therefore well suited for single use.

The invention further relates to a valve, which may comprise a valve housing and a gas-filled resilient body fittingly arranged therein.

In one embodiment, the valve housing may have an inflow opening and an outflow opening, and the gas-filled resilient body may be arranged to close off a flow path between the inflow and outflow openings.

In a further embodiment, the valve may further comprise an operating member that may be engageable with the gas-filled resilient body to deform it so that the flow path is freed.

In yet another embodiment, the valve housing may have an internal volume that is variable so as to apply a predetermined pressure on the gas-filled resilient body. By adjusting the pressure inside the resilient body in this way, the valve may be pre-tensioned or biased, so that it will require a higher or lower pressure to open.

The invention also relates to a spring, which may comprise a spring housing and a gas-filled resilient body arranged therein so as to allow the housing to expand or retract. The housing may be flexible, or it may consist of two or more pieces which are moveable with respect to each other.

In one embodiment the gas-filled resilient body may be configured to have a predetermined spring characteristic.

In a further development, a plurality of gas-filled bodies may be arranged in the spring housing so as to provide the predetermined spring characteristic.

Alternatively or additionally, the gas-filled resilient body may include a plurality of chambers which may be arranged in the spring housing so as to provide the predetermined spring characteristic.

The invention further relates to a rapid-action dispensing device, which may comprise means for pressurizing a liquid to be dispensed, an outlet opening closed off by a manually operable valve, and a gas-filled resilient body arranged in a buffer housing between the pressurizing means and the outlet so as to buffer the pressurized liquid in the housing by compressing the gas-filled resilient body until the valve is manually opened. Using the gas-filled resilient body as a buffer in such a device allows the liquid to be readied for dispensing by being pressurized and then being stored under pressure until the moment that the liquid is to be dispensed. This may be advantageous in situations where there is no opportunity to pressurize the liquid during dispensing, e.g. when the liquid has to be injected into a body. Moreover, in this way the pressure at which the liquid is dispensed is more consistent and less user-dependent than in a regular dispensing device where liquid is dispensed by a user operating a plunger.

The invention also relates to a dispensing device, which may comprise a housing having an outlet opening, a resilient body partially filled with gas and partially filled with a material to be dispensed, and a piercing member for piercing the resilient body so as to allow the material to be urged out by the gas, wherein the piercing member and the resilient body are movable with respect to each other. Such a dispensing device, where the material to be dispensed is packed in the resilient body together with its propellant—the gas— is instantly ready for use. Moreover, such a dispensing device may be structurally simple and low cost. The housing may enclose the resilient body, or it may be connected to a part of the resilient body. The piercing member may be movable and the resilient body stationary, or the other way around.

In an embodiment of this dispensing device the piercing member may be tubular and may extend through the outlet opening. The piercing member may e.g. be a hollow needle which may have sharp tip at its end opposite the resilient body which may be used to inject the material through the skin of a body.

In all embodiments of the invention described above the gas-filled resilient body may be substantially cylindrical or it may be a body of revolution, e.g. a toroid ("donut") or a lens-shaped body. In some embodiments the gas-filled resilient body may be conical or "Christmas tree" shaped in side view while having a substantially circular cross-section.

The invention will now be illustrated by way of a number of exemplary embodiments, with reference being made to the annexed drawings, in which.

Figure 1A:
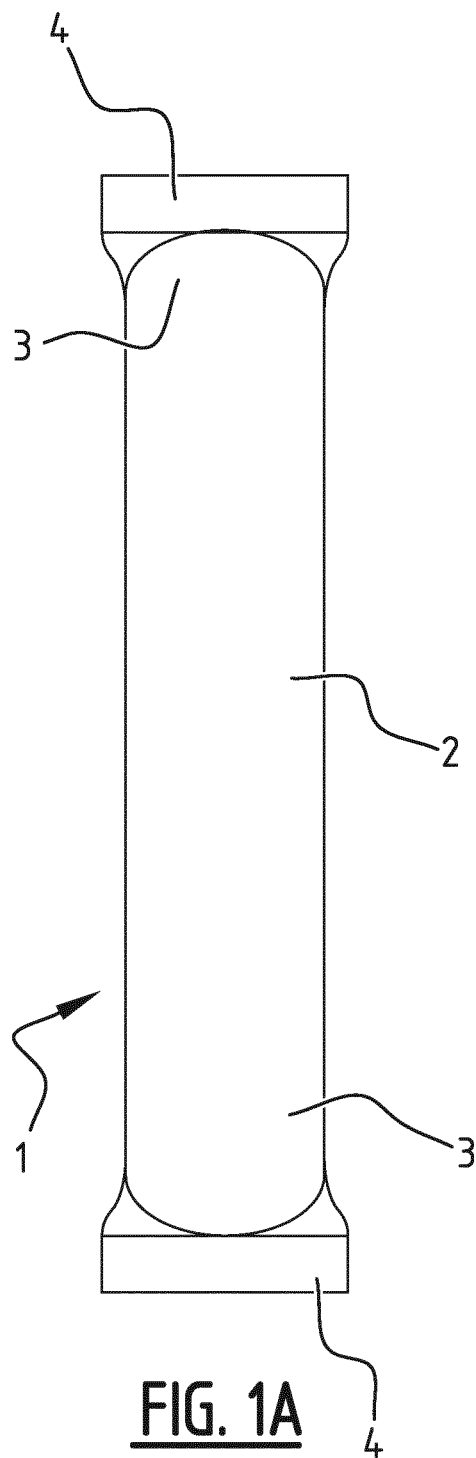
FIGS. 1A and 1B show a front view and a side view, respectively, of a gas-filled resilient body made from a tube in accordance with an embodiment of the invention.
Figure 1B:
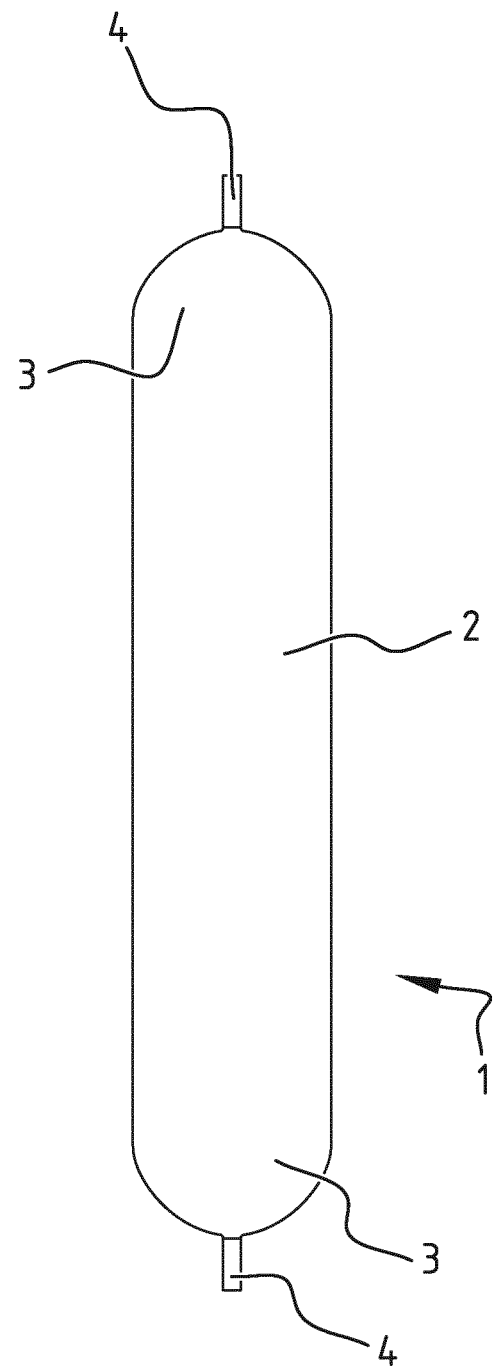
Figure 3A:
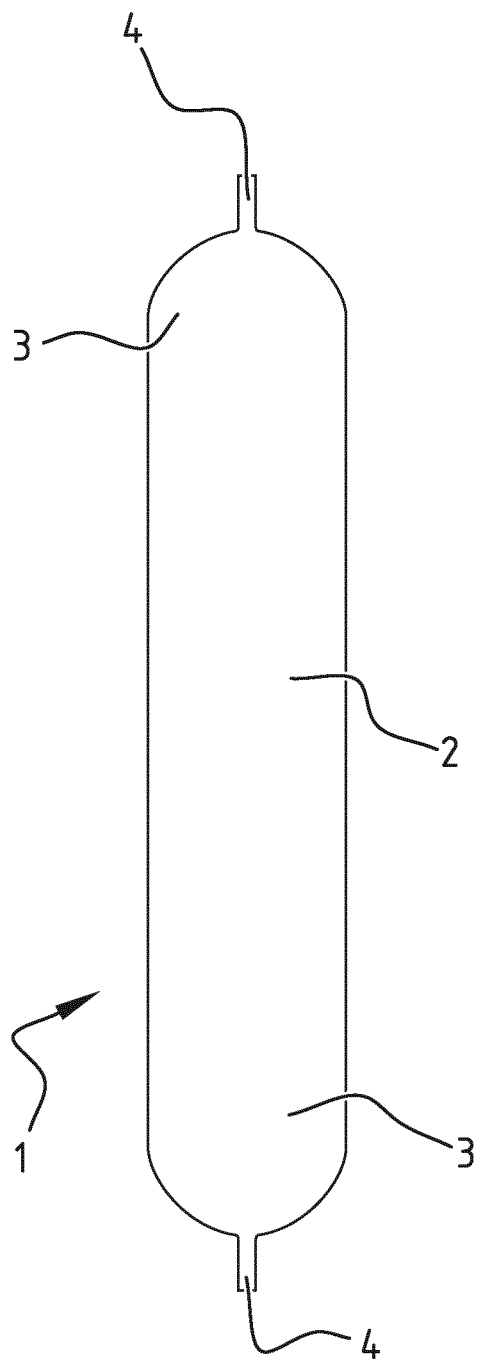
FIGS. 3A and 3B show a front view and a side view, respectively, of a gas-filled resilient body made from a tube in accordance with yet another embodiment of the invention.
Figure 3B:
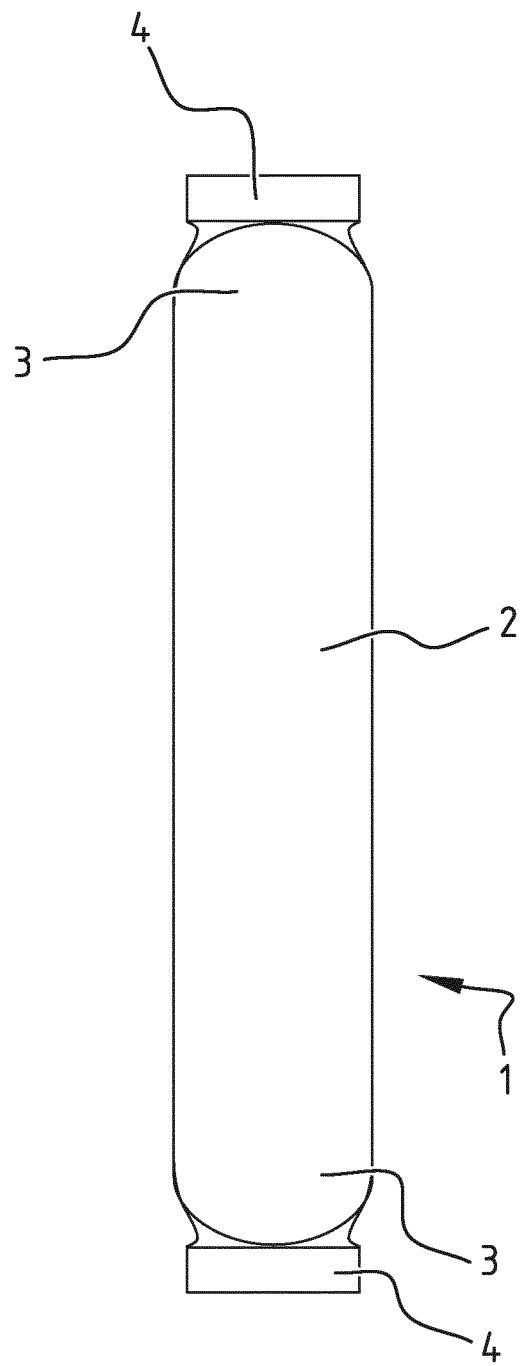
Figure 4A:
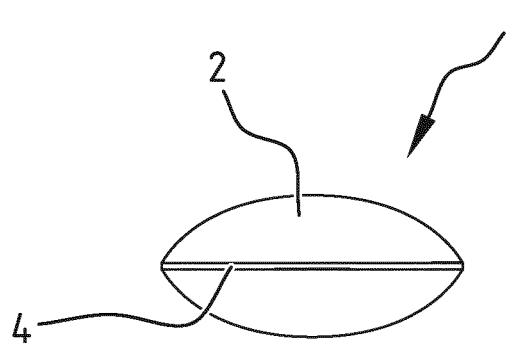
Figure 4B:
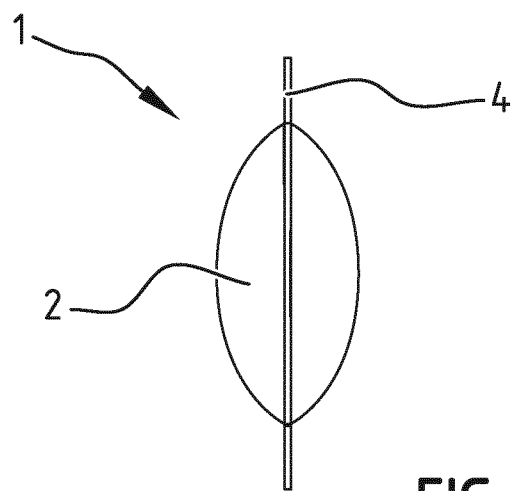
Figure 4C:
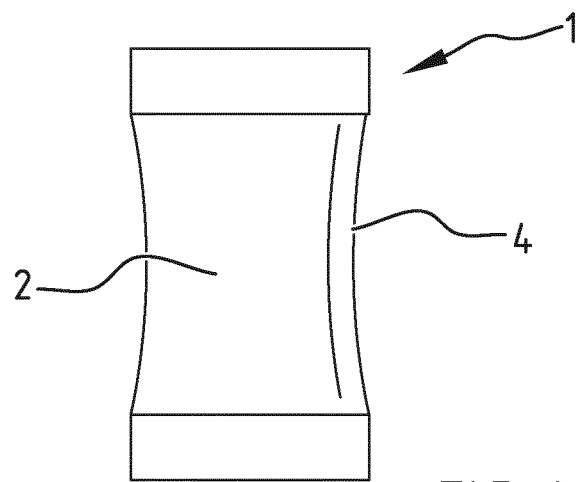
Figure 5A:
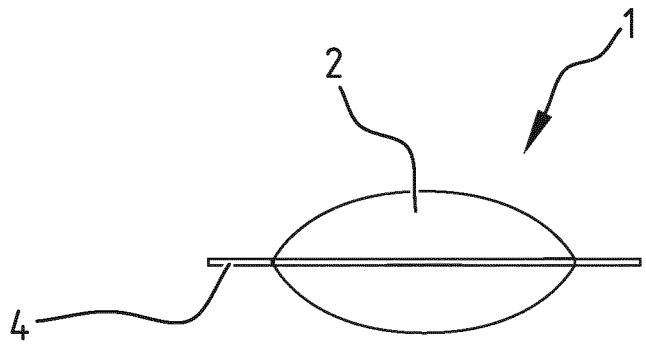
Figure 5B:
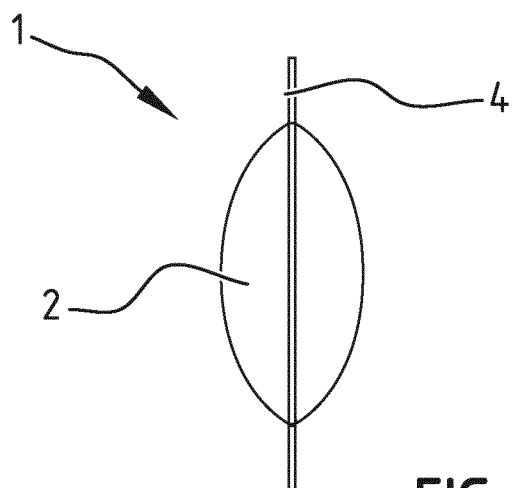
Figure 5C:
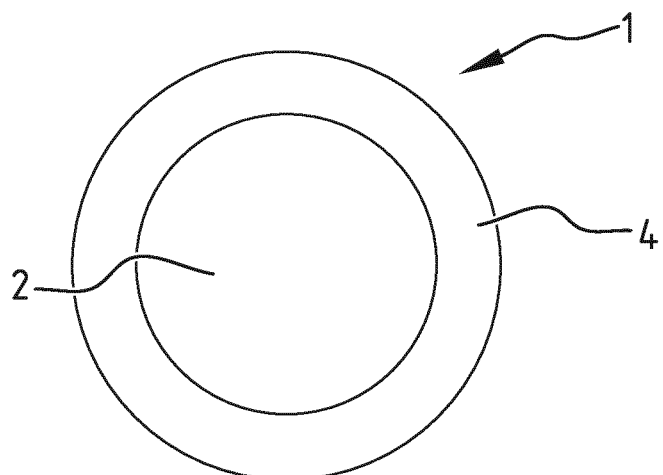
Figure 6A:
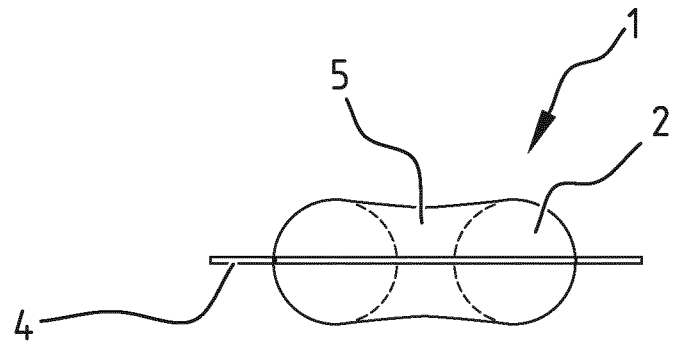
Figure 6B:
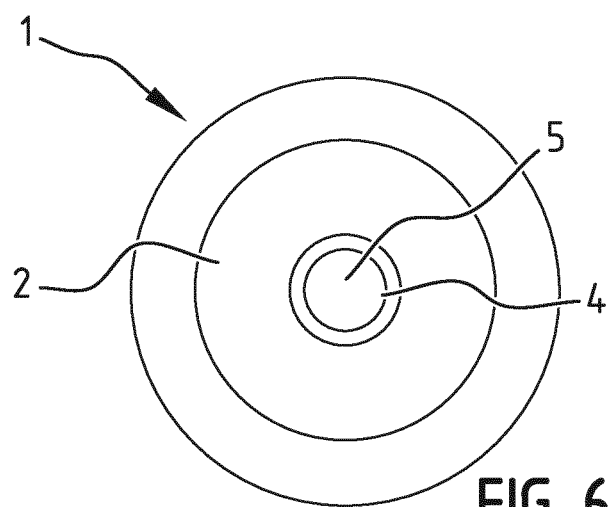
Figure 6C:
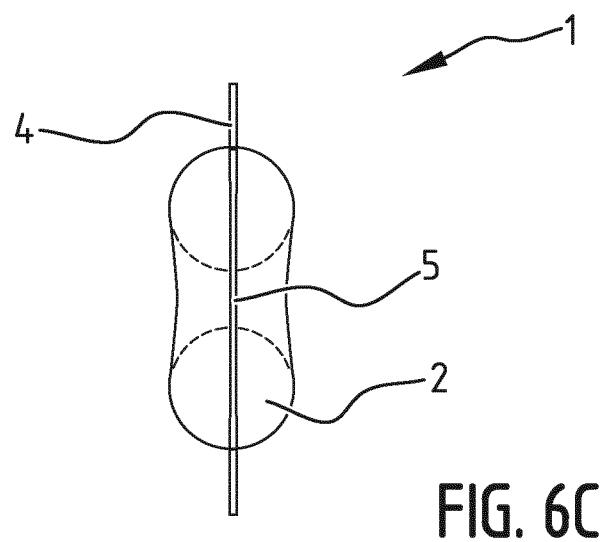
Figure 7:
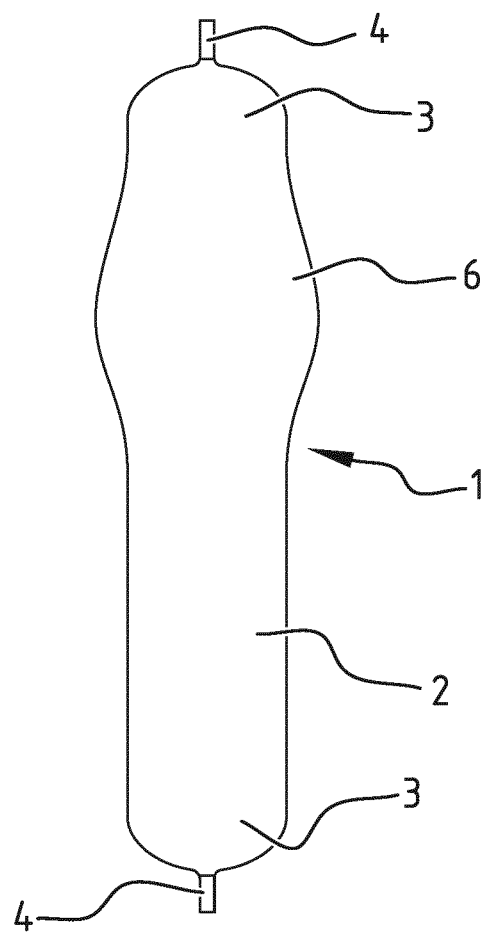
Figure 8:
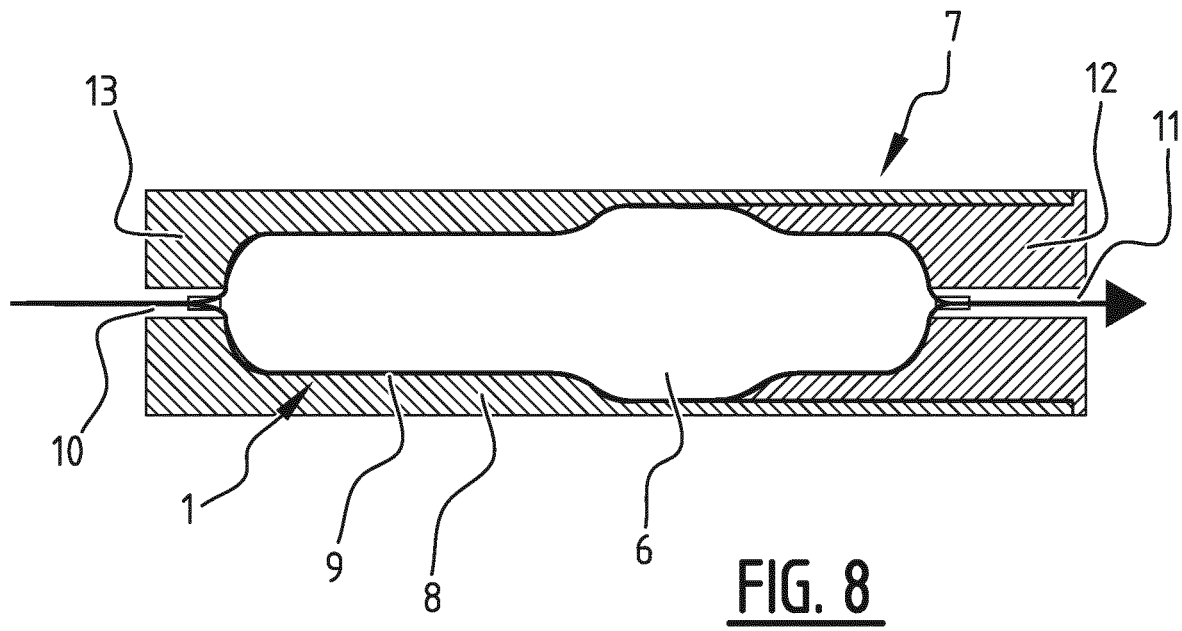
Figures 9, 10:
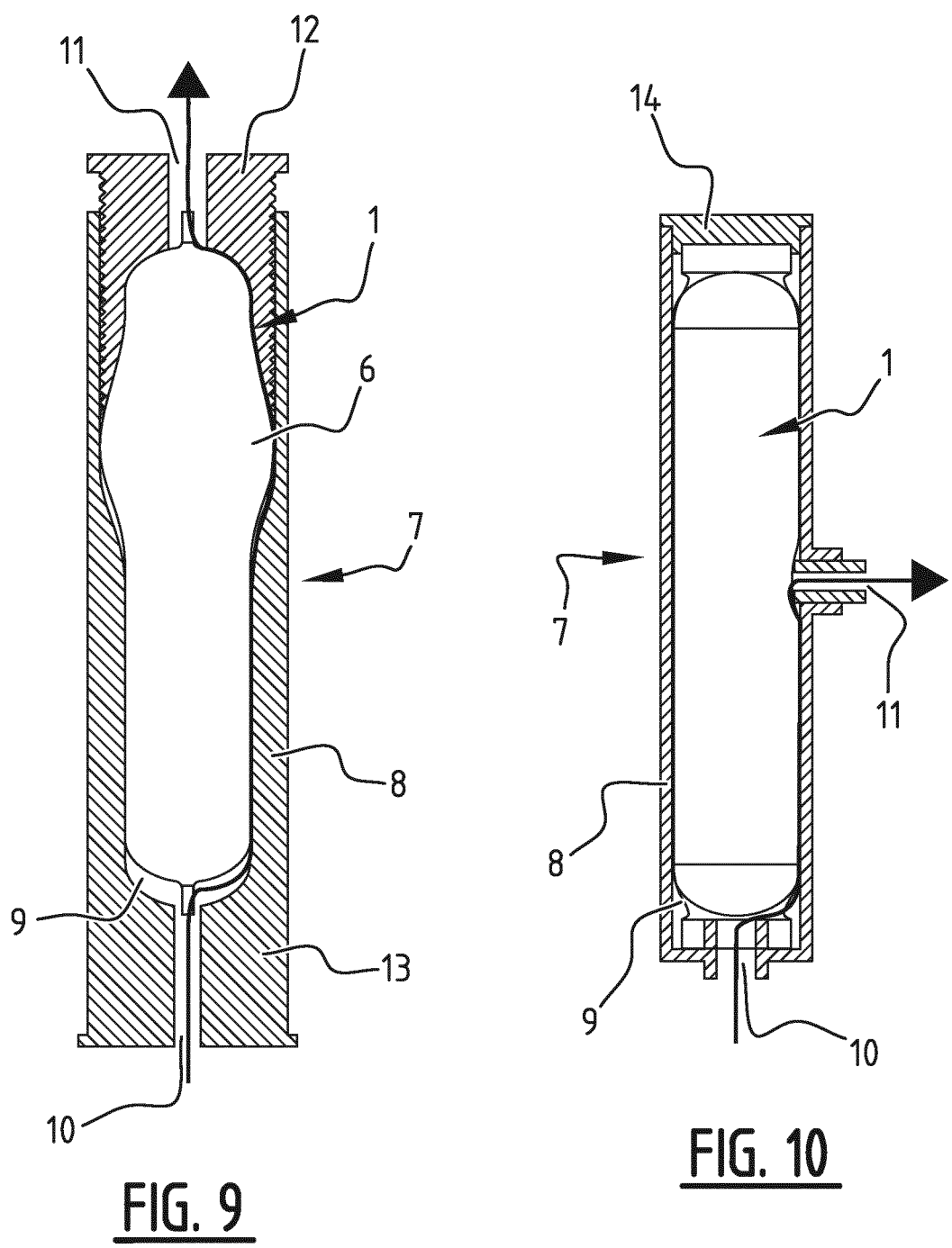
Figure 11:
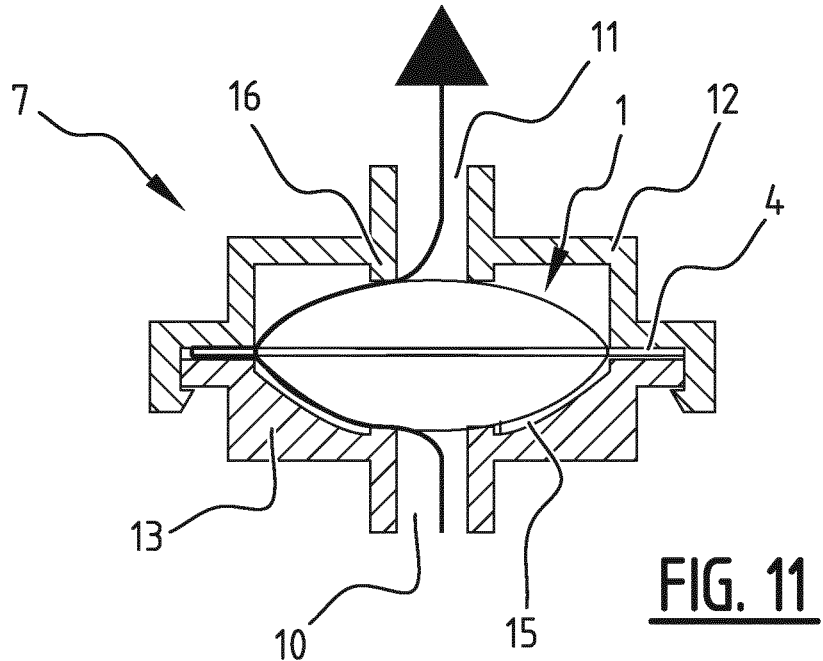
Figure 12:
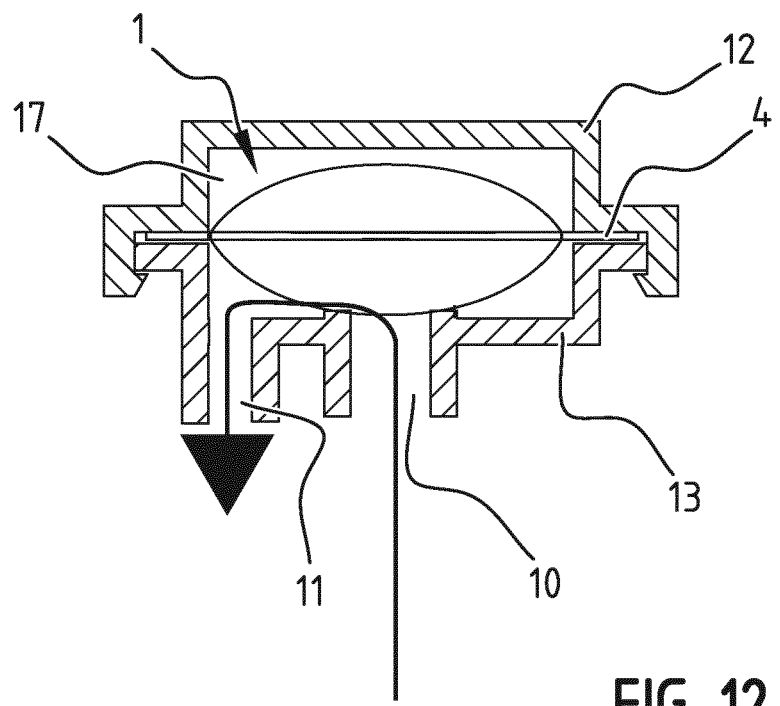
Figure 13A:
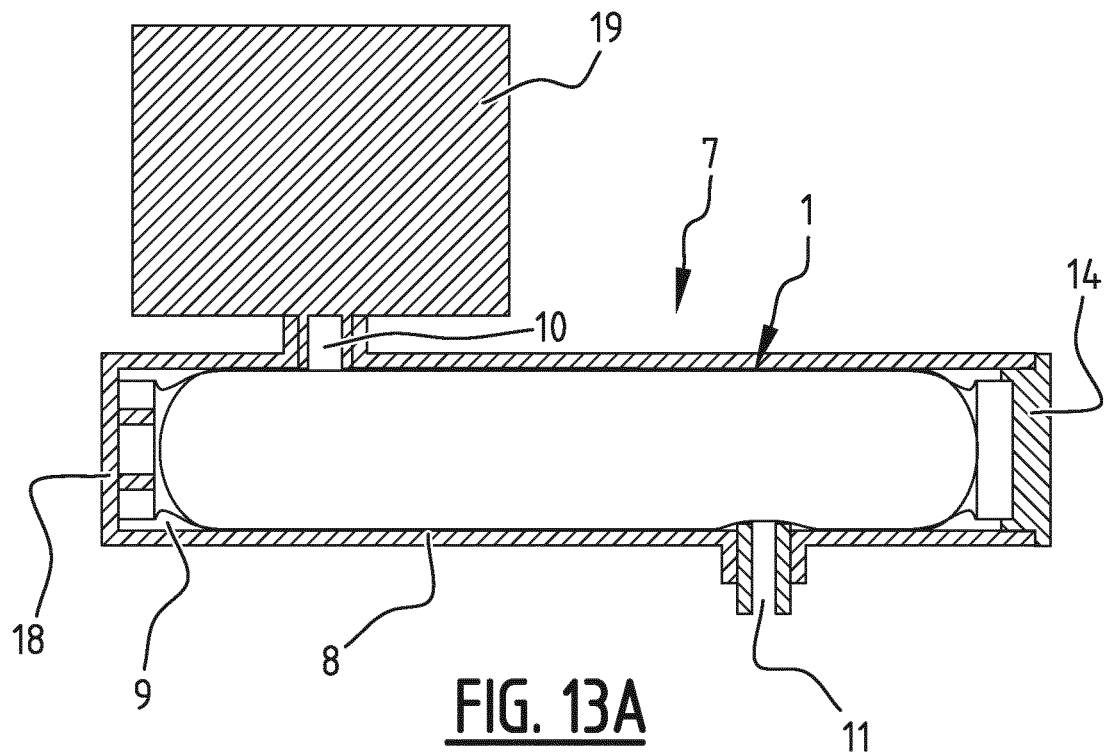
Figure 13B:
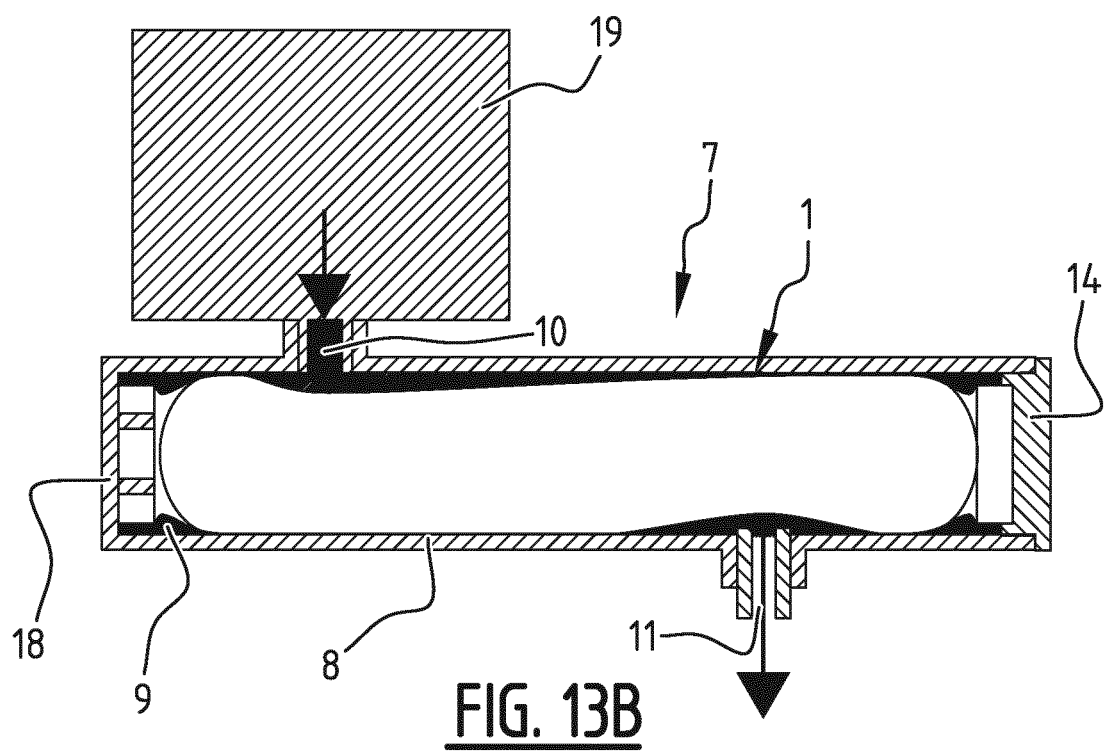
Figure 14B:
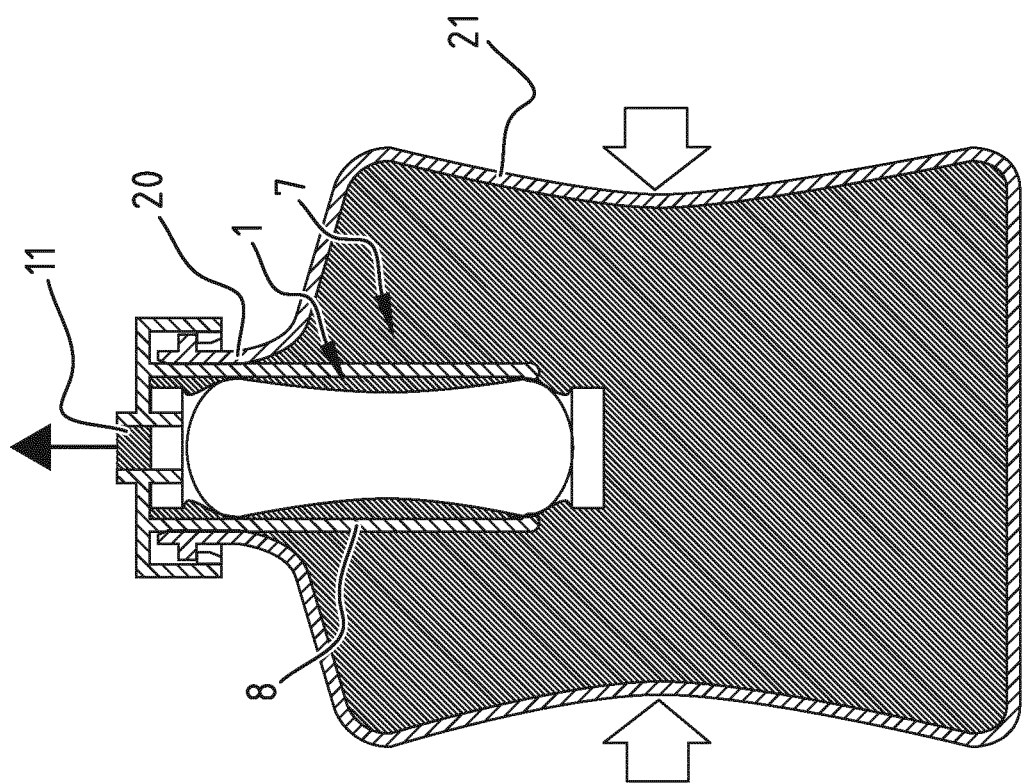
Figure 14A:
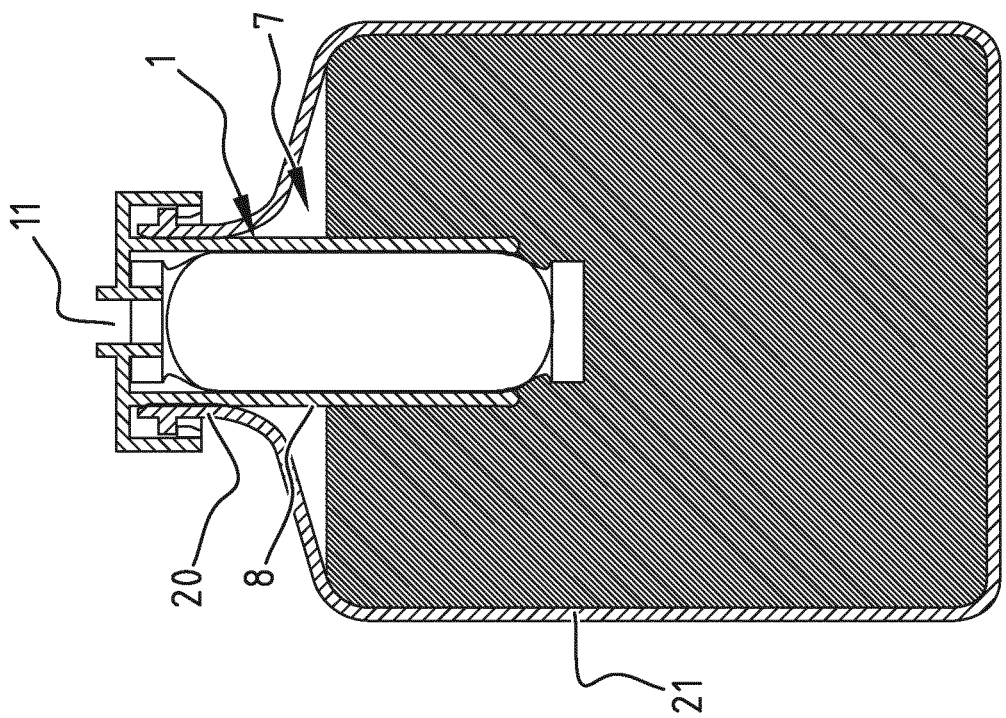
Figure 15B:
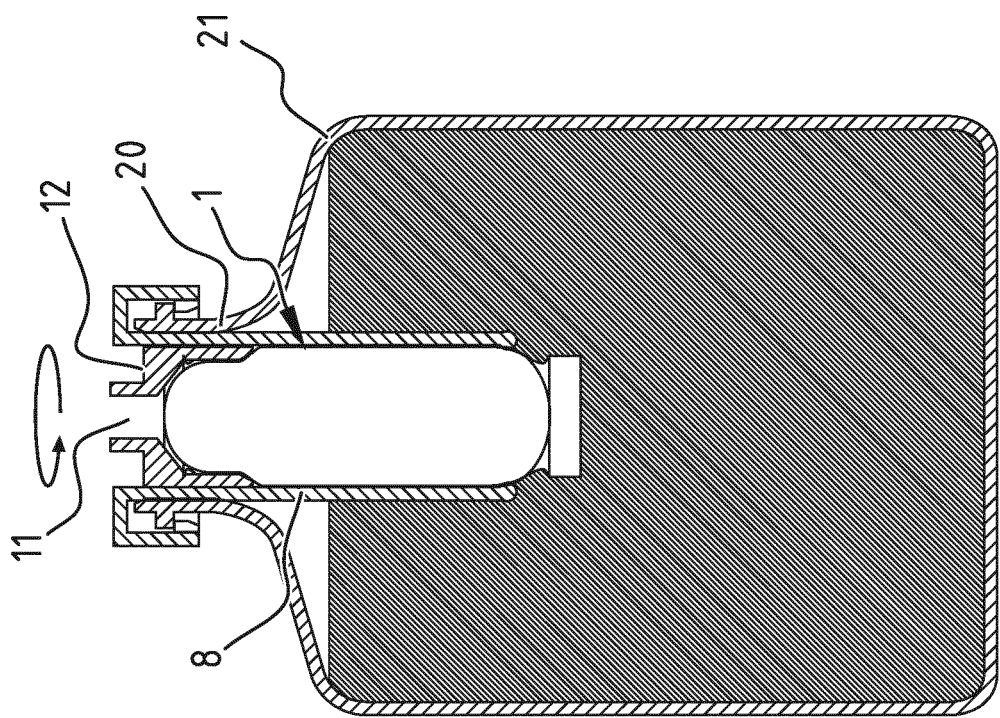
Figure 15A:
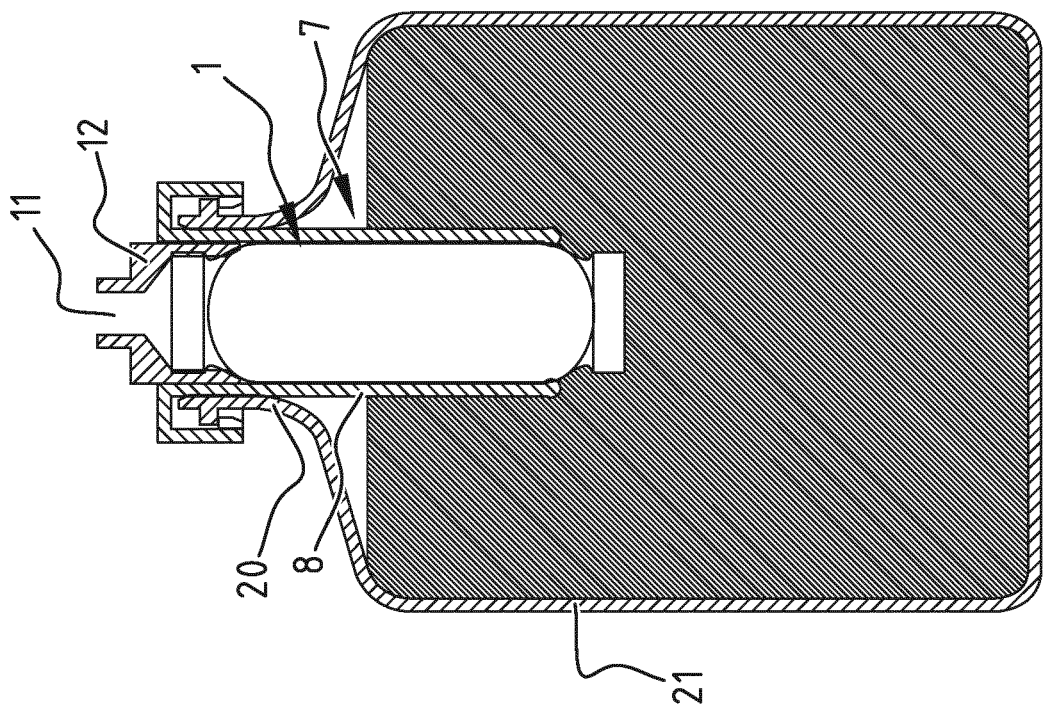
Figure 16A:
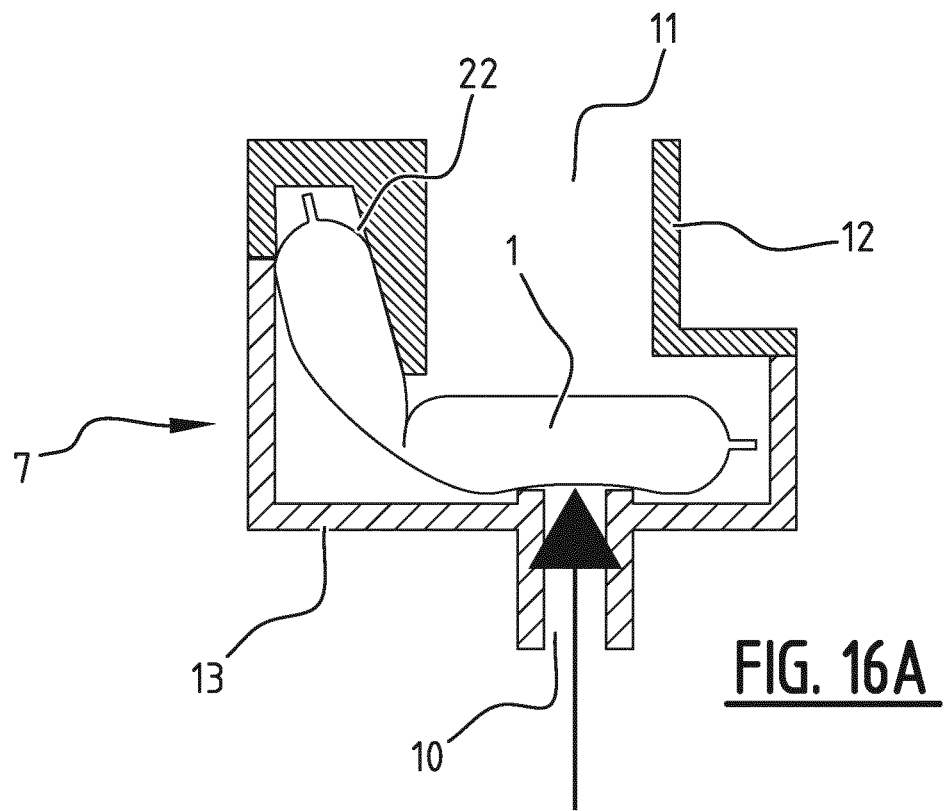
Figure 16B:
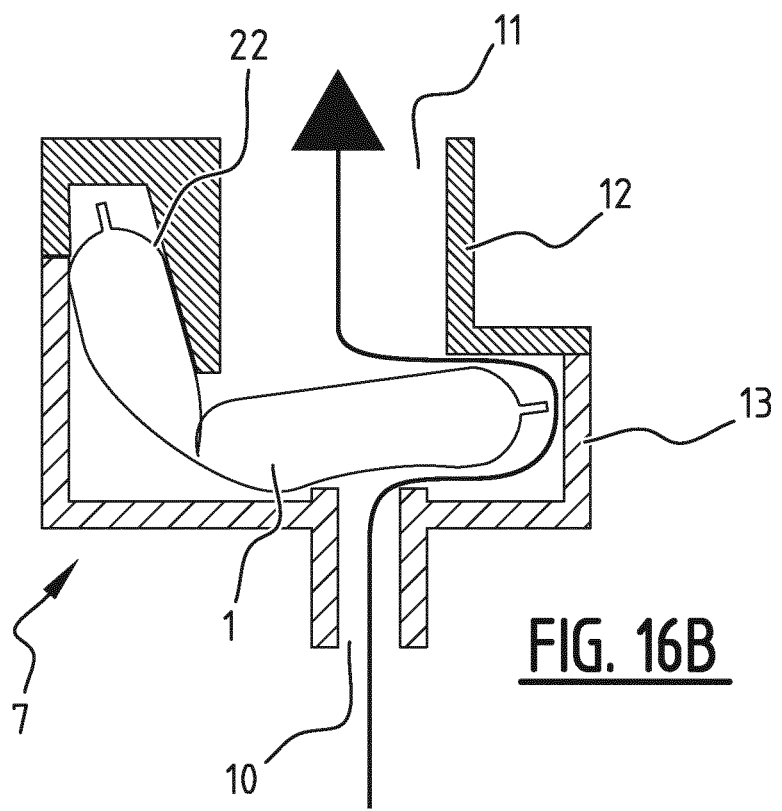
Figure 17A:
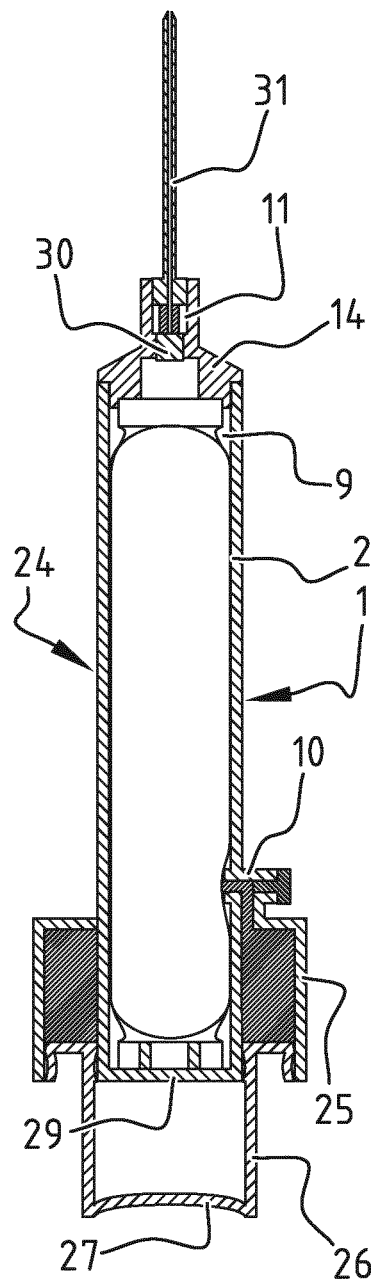
Figure 17B:
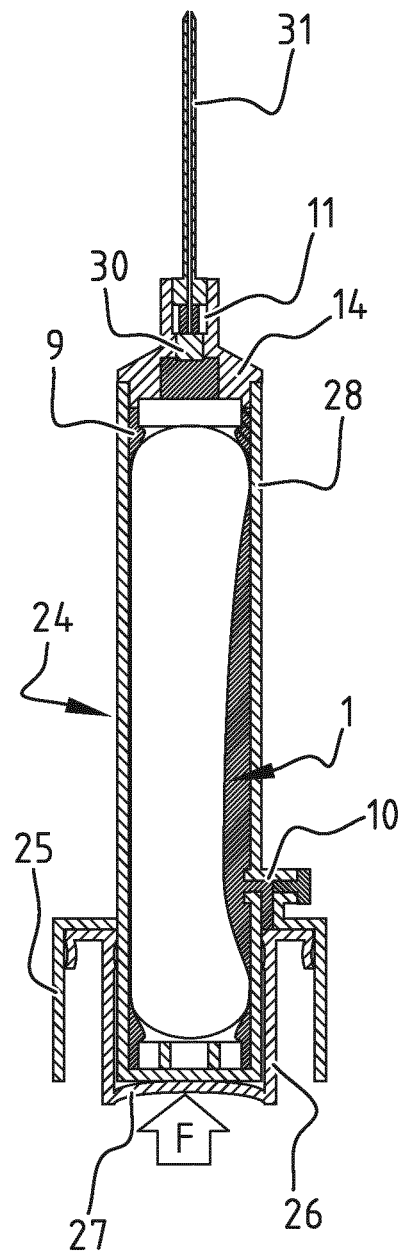
Figure 17C:
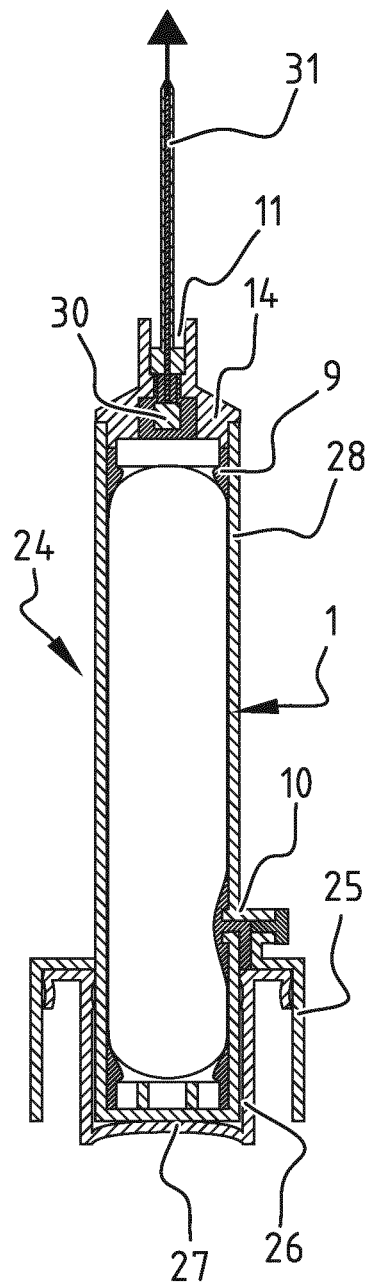
Figure 18C:
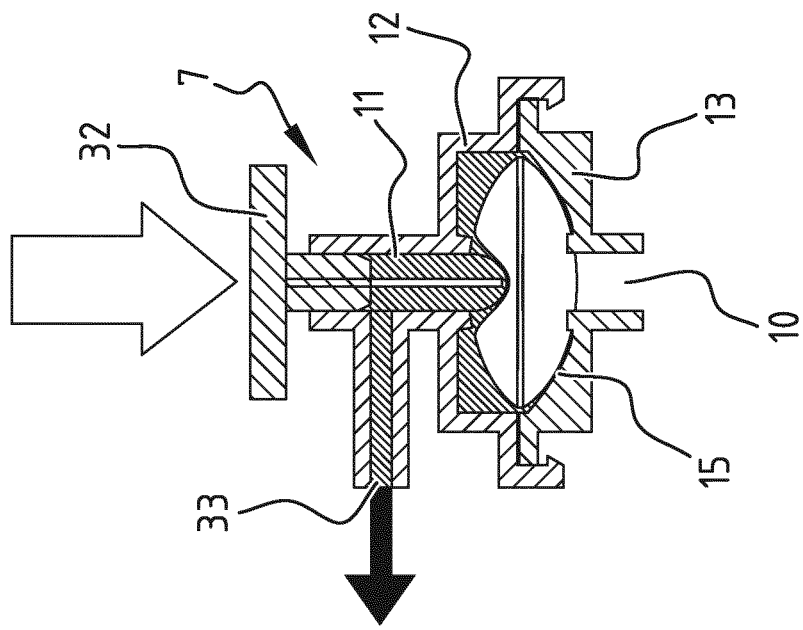
Figure 18B:
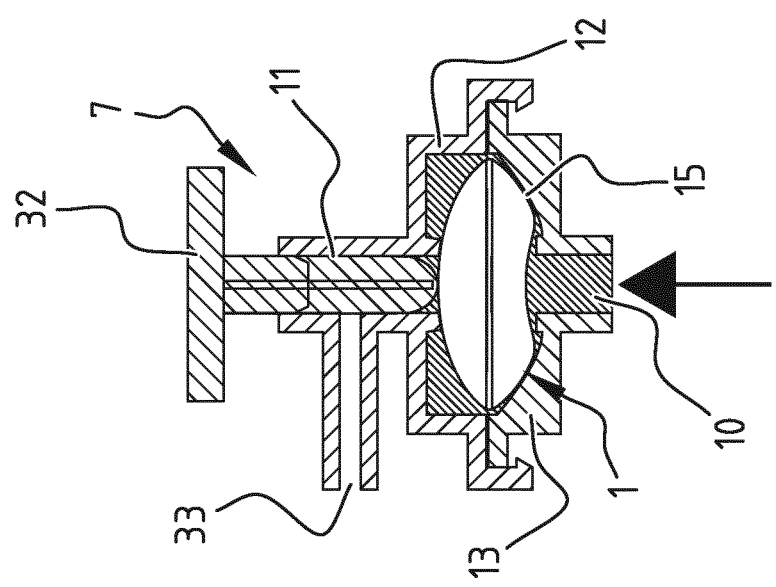
Figure 18A:
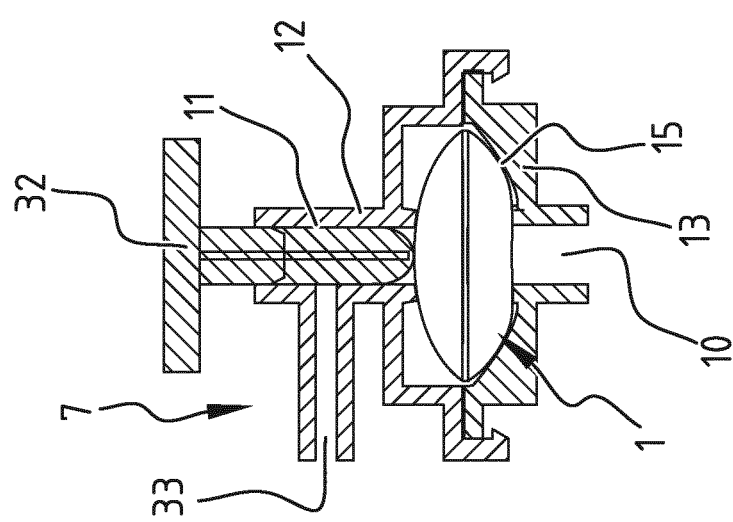
Figures 19A, 19B:
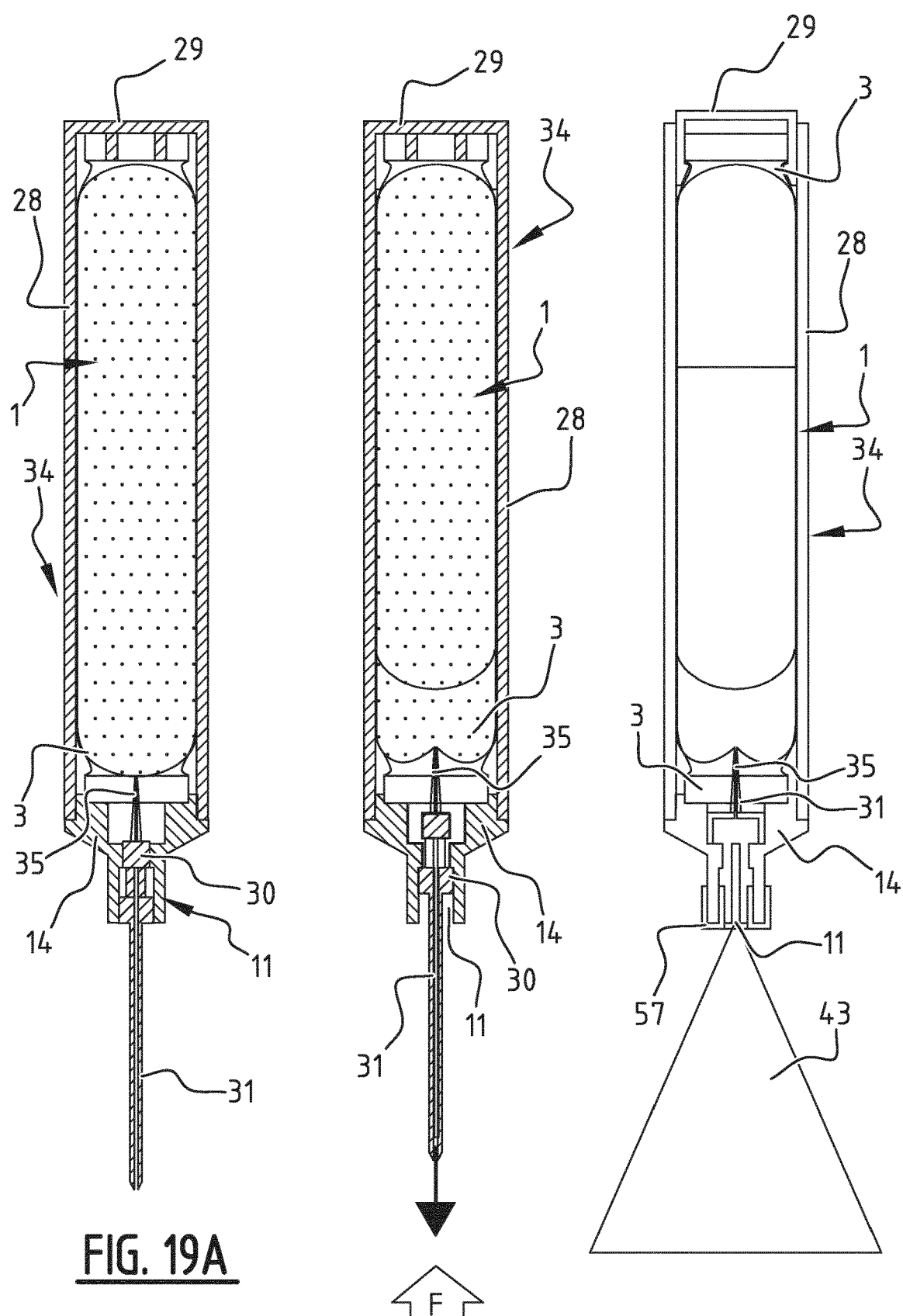
Figure 20A:
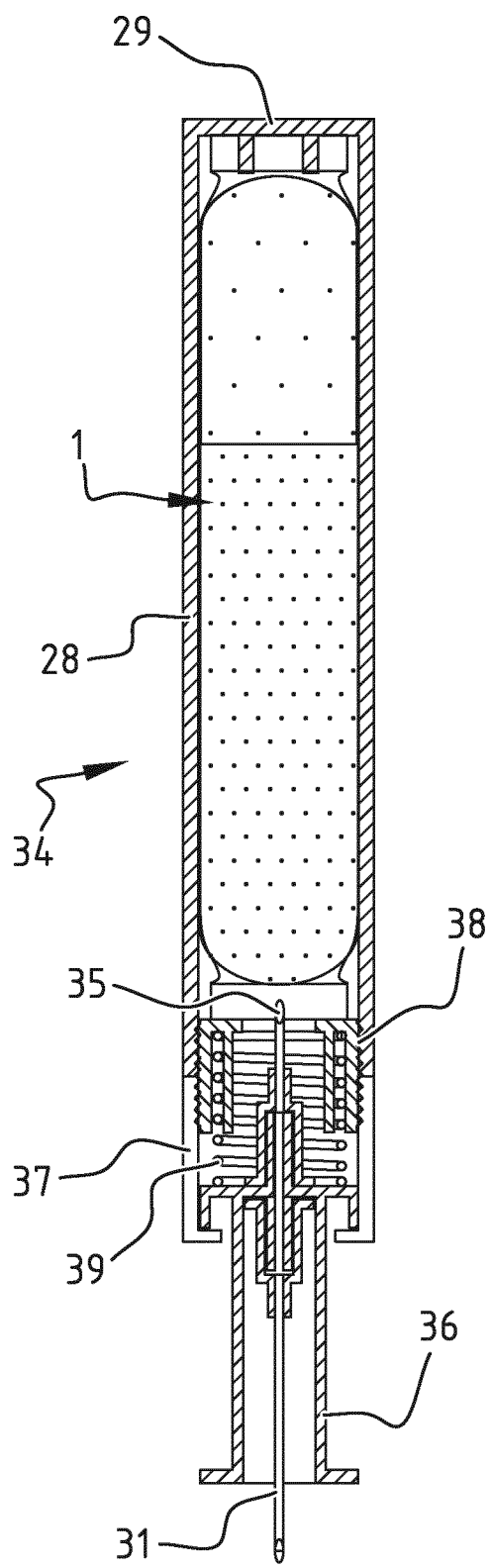
Figure 20B:
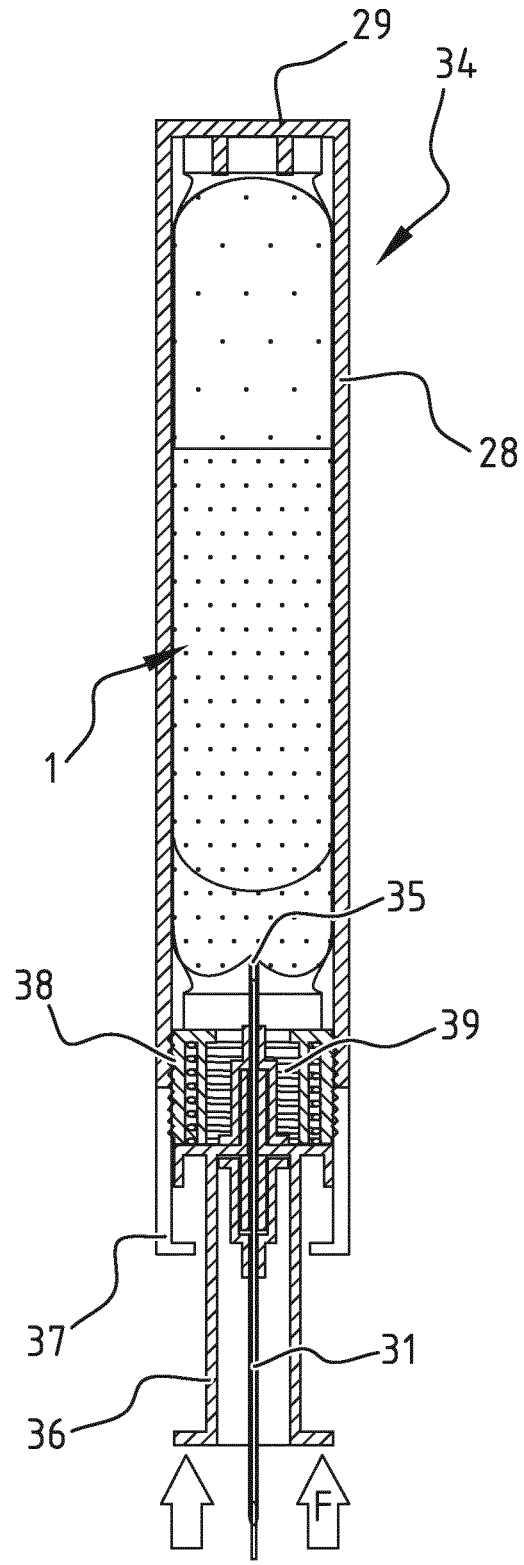
Figure 20C:
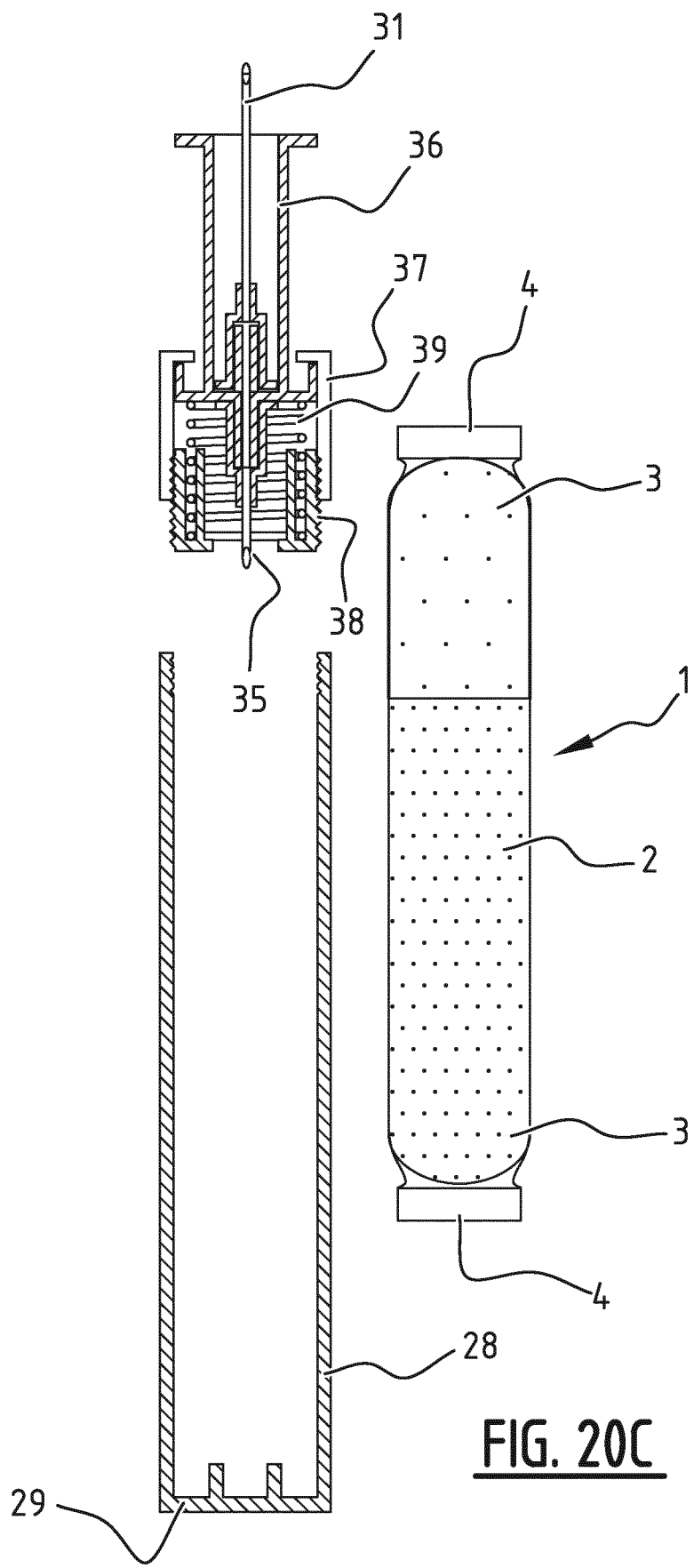
Figure 23A:
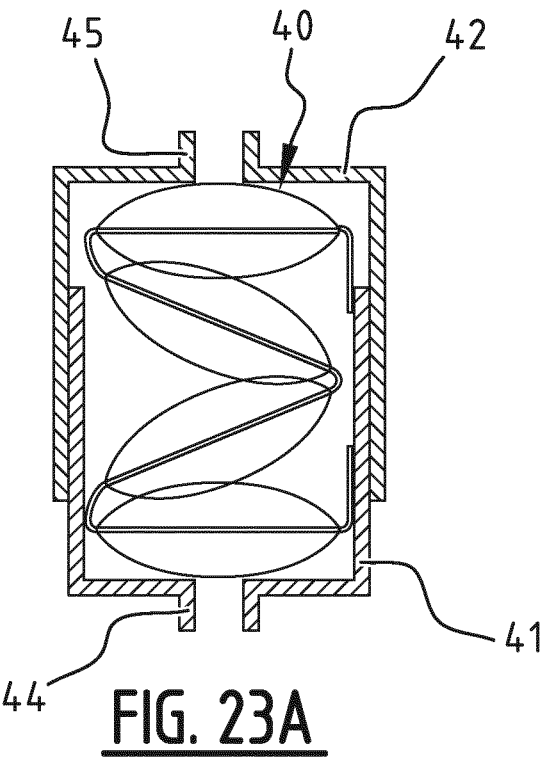
Figure 23B:
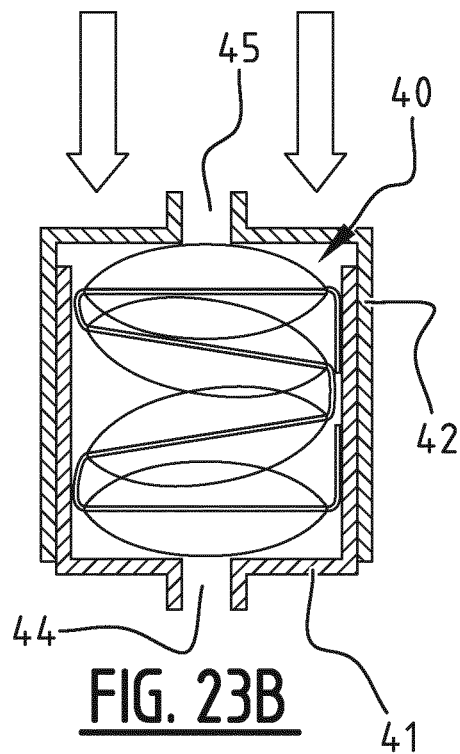
Figure 24A:
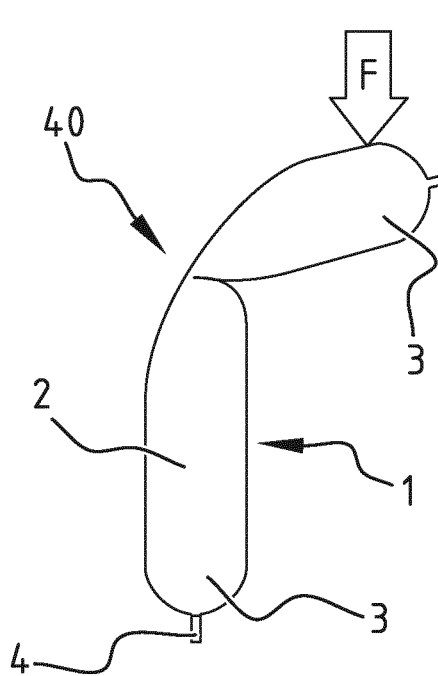
Figure 24B:
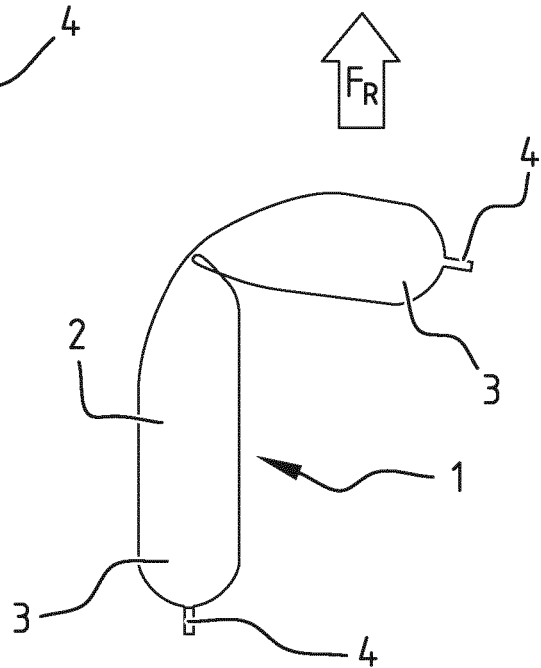
Figure 25A:
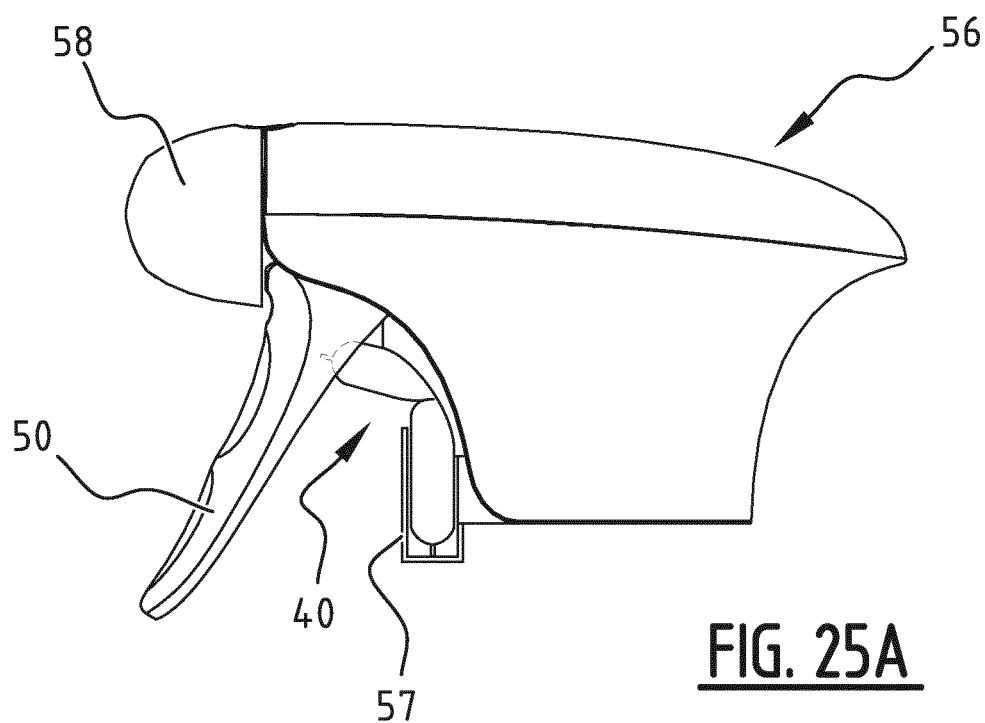
Figure 25B:
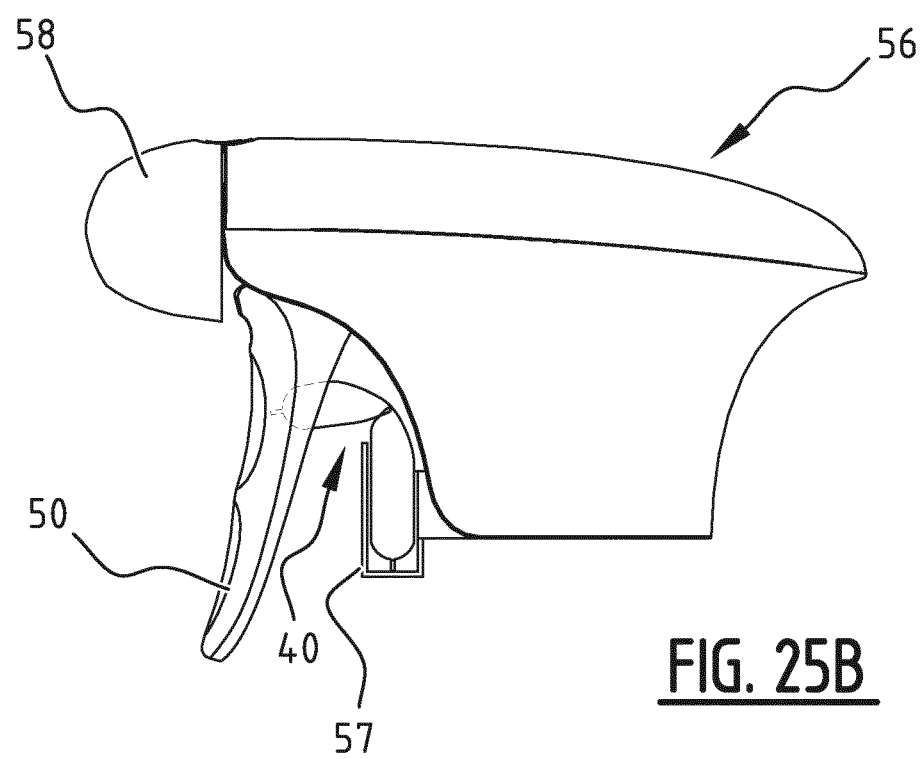
Figure 26:
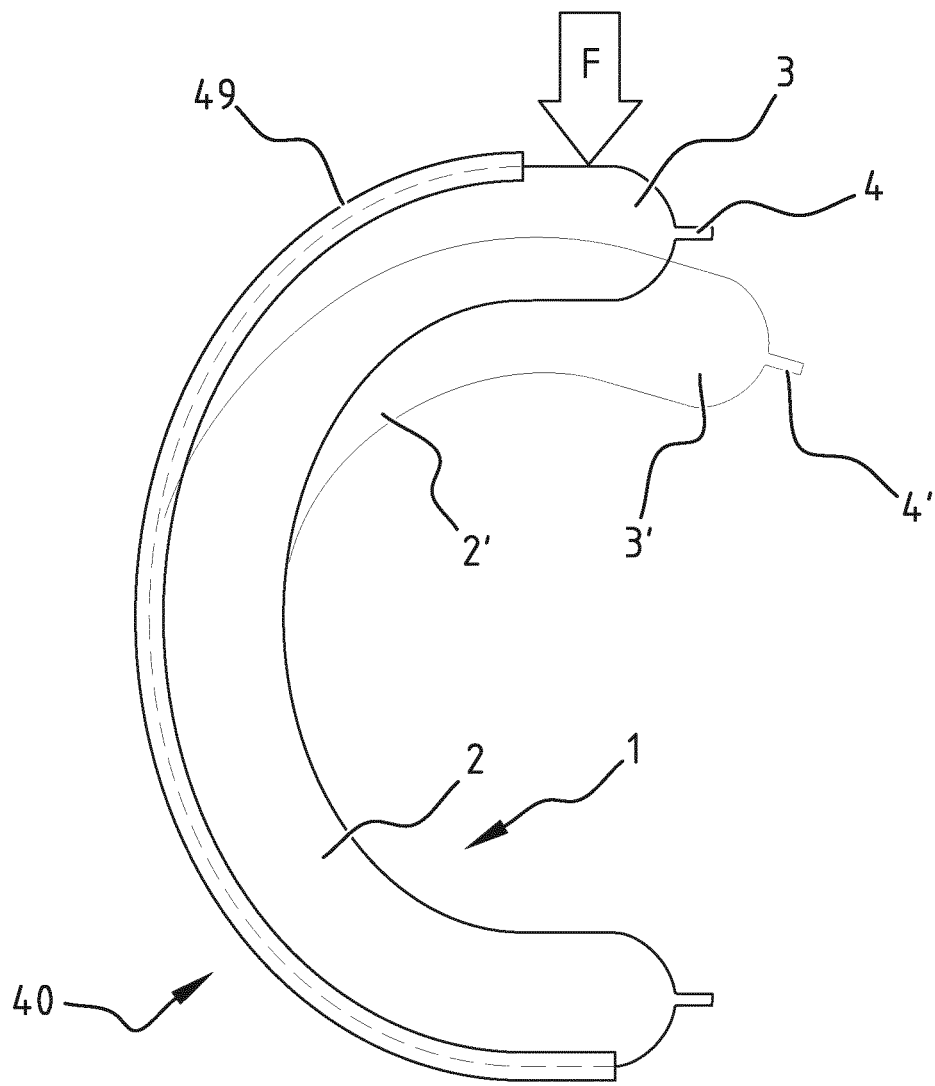

FIGS. 4A-C show side views from mutually perpendicular directions and a top view, respectively, of a gas-filled resilient body made from two layers of sheet material in accordance with an embodiment of the invention;

FIGS. 5A-C show views corresponding with FIGS. 4A-C of a gas-filled resilient body made from two layers of sheet material in accordance with another embodiment of the invention;

FIGS. 6A-C show views corresponding with FIGS. 4A-C and FIGS. 5A-C of yet another embodiment of a gas-filled resilient body made from two layers of sheet material;

FIG. 7 is a side view of a substantially cylindrical gas-filled resilient body which has been locally widened by blow molding or hydroforming;

FIG. 8 is a longitudinal sectional view of a variable volume valve in accordance with an embodiment of the invention and including the gas-filled resilient body of FIG. 7 as valve member;

FIG. 9 is a view corresponding with FIG. 8 and showing the valve after its internal volume has been increased to reduce the pressure inside the gas-filled resilient body and the opening pressure of the valve;

FIG. 10 is a longitudinal sectional view of a valve in accordance with another embodiment of the invention and including the gas-filled resilient body of FIG. 3 as valve member;

FIG. 11 is a longitudinal sectional view of an overpressure valve in accordance with an embodiment of the invention and including the gas-filled resilient body of FIG. 5 as valve member;

FIG. 12 is a longitudinal sectional view of another valve in accordance with the invention which includes the same gas-filled resilient body of FIG. 5 as valve member;

FIGS. 13A and 13B are longitudinal sectional views of a pre-compression buffer valve in accordance with yet another embodiment of the invention and including the gas-filled resilient body of FIG. 3 as valve member, showing the valve in closed and open positions, respectively;

FIGS. 14A and 14B are longitudinal sectional views of a dispensing device in accordance with an embodiment of the invention including an outlet valve on the basis of the gas-filled resilient body of FIG. 3, showing the valve in closed and open positions, respectively;

FIGS. 15A and 15B are longitudinal sectional views of a variant of the dispensing device of FIG. 14 having a valve housing with variable volume to adjust a pressure at which the valve opens;

FIGS. 16A and 16B are longitudinal sectional views of a valve in accordance with yet another embodiment of the invention and including the gas-filled resilient body of FIG. 1 in bent shape as valve member, showing the valve in closed and open positions, respectively;

FIGS. 17A-C are longitudinal sectional views of a rapid-action dispensing device in accordance with an embodiment of the invention and having the gas-filled resilient body of FIG. 3 as buffer member, shown in a position of rest, in a standby position with pressurized liquid deforming the body, and during dispensing, respectively;

FIGS. 18A-C are longitudinal sectional views of a metered overpressure valve in accordance with yet another embodiment of the invention and including the gas-filled resilient body of FIG. 5 as valve member, showing the valve in closed position, in an intermediate position in which the valve housing is filled with liquid, and after operating an external member to relieve the overpressure, respectively;

FIGS. 19A and 19B are longitudinal sectional views of a dispensing device in accordance with an embodiment of the invention and including the partially gas-filled resilient body of FIG. 3 acting as a container, showing the device in a standby position and during dispensing, respectively;

FIG. 19C is a view corresponding with FIGS. 19A and 19B of an alternative embodiment of the dispensing device;

FIGS. 20A and 20B are views corresponding with FIGS. 19A and 19B of a further embodiment of the dispensing device, while FIG. 20C is an exploded view of the dispensing device;

FIGS. 21A and 21B are longitudinal sectional views of an applicator in accordance with an embodiment of the invention;

FIGS. 22A and 22B show a longitudinal sectional view and a side view in folded state, respectively, of a spring in accordance with an embodiment of the invention, having a plurality of gas-filled resilient bodies of FIG. 4 as chambers;

FIGS. 23A and 23B are side views of the spring of FIG. 22 in a spring housing, shown in uncompressed and in compressed state, respectively;

FIGS. 24A and 24B are side views of a gas-filled resilient body of FIG. 1 in bent shape to form a spring, showing two stages of bending;

FIGS. 25A and 25B are side views of a trigger sprayer mechanism including the gas-filled resilient bodies in bent shape as springs; and FIG. 26 is a side view of a gas-filled resilient body of FIG. 1 held in curved shape by a flexible support member to form a C-spring, shown both in uncompressed and in compressed state.

A tubular gas-filled resilient body 1 (FIG. 1) may be manufactured by providing a tube 2 made from a plastics material, sealing it at a first end 3, filling the tube 2 with a pressurized gas and then sealing it at a second end 3 opposite the first end 3. The tube 2 may be made from any suitable plastics material, and may include multiple layers made from different materials, such as e.g. PE, PP, EVOH, (functionalized) polyolefins, or any other material having suitable characteristics, like e.g. barrier properties, strength, resiliency, etc. The tube 2 may be made by extrusion, by injection molding or by rolling and welding sheet material. When using injection molding the tube 2 could be formed with a closed bottom, like a test tube. In that case it could be filled straight away and would only have to be sealed at one end. The tube 2 may be sealed by a simple transverse weld 4, which will extend somewhat outside the tube 2.

Figure 2A:
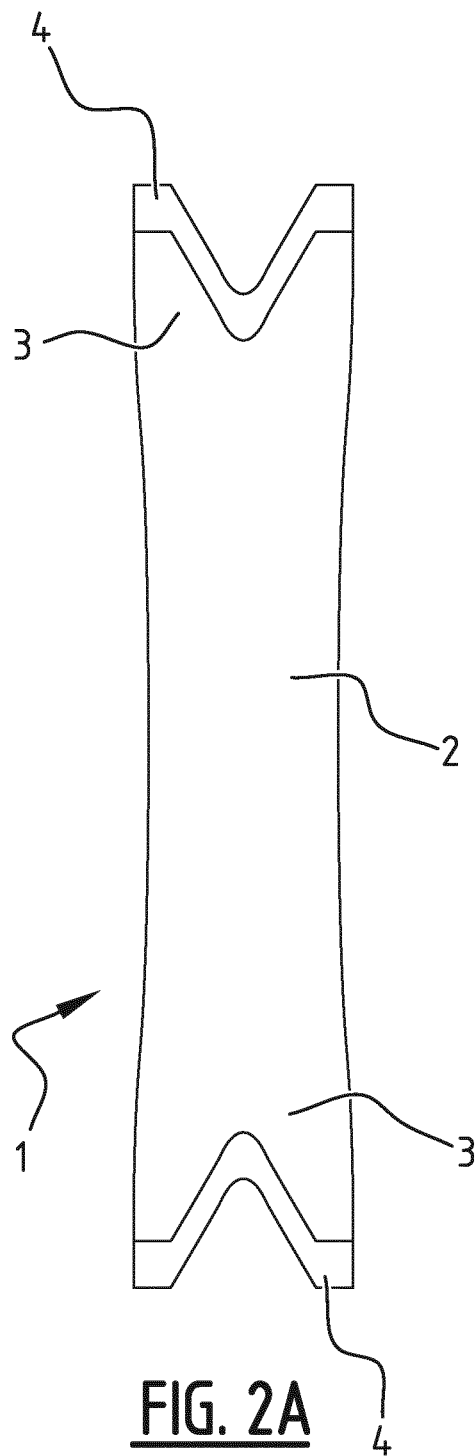
FIGS. 2A and 2B show a front view and a side view, respectively, of a gas-filled resilient body made from a tube in accordance with another embodiment of the invention.
Figure 2B:
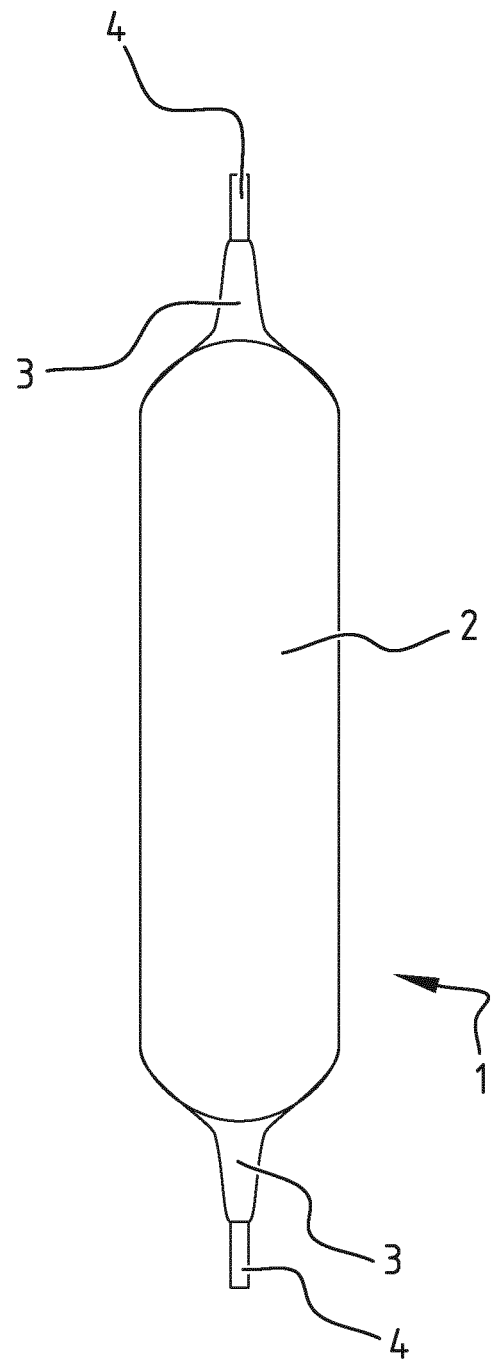

For applications where the diameter of the tube 2 should not be exceeded by the weld, a special V-shaped weld 4 may be formed (FIG. 2). This will cause a slight reduction in the useful volume of the gas-filled resilient body 1, due to the inwardly directed shape of the weld 4.

Another way to prevent the weld 4 from extending outside the tube 2 is by increasing the diameter of the tube 2 (FIG. 3).

Instead of being tubular, a gas-filled resilient body 1 may also have a relatively flatter shape. For instance, the body 1 may be pillow-shaped (FIG. 4). Such a pillow shape may be formed either by placing two sheets of material on top of each other and sealing them along their entire edges, or by folding a single sheet and then sealing it along the loose edges 4, as shown in the Figure. After sealing the edges 4, a small opening is maintained through which the gas may be injected to inflate the pillow. This opening is then sealed as well.

The pillow may have any desired shape, and may e.g. be circular (FIG. 5). Such a circular pillow may be formed by sealing two circular sheets along their periphery.

In another embodiment the sheets are not just sealed at their periphery, but at their center as well. A hole 5 may be formed in the center of the sheets of material before or after sealing, so that the final shape of the body 1 after injecting a pressurized gas is toroidal ("donut").

When a tubular gas-filled resilient body 1 is used as starting point, this may be further formed into a more complex shape, e.g. a shape having a local bulge or shoulder 6, which may be more effective for certain applications. This further shaping may be done e.g. by blowing or hydroforming.

The gas-filled resilient body 1 having the shoulder 6 may be used as a valve member in an adjustable pressure outlet valve 7 (FIG. 8). This valve 7 includes a valve housing 8 defining a cavity 9 in which the gas-filled resilient body 1 may be accommodated. The valve housing 8 has an inflow opening 10 and an outflow opening 11. In a position of rest, the valve member or gas-filled resilient body 1 blocks a flow path between the inflow and outflow openings 10, 11. When a fluid F at the side of the inflow opening 10 reaches a pressure that is higher than the gas pressure inside the body 1, the fluid will flow into the inflow opening 10, through the cavity 9 around the gas-filled resilient body 1 and out of the outflow opening 11. During its passage through the cavity 9 and around the body 1, the fluid will compress the body 1 to free the flow path from the inflow opening 10 to the outflow opening 11. When the fluid pressure falls below the internal gas pressure, the gas pressure inside the resilient body 1 will again cause the body to expand until it reaches the walls of the cavity 9 and blocks the flow path.

In this embodiment the valve 7 has an adjustable opening pressure or "cracking pressure". Adjustment of the opening pressure is achieved by varying the volume of the cavity 9, thus varying the pressure acting on the gas inside the resilient body 1. When the volume of the cavity is increased (FIG. 9), the resilient body 1 may expand and the pressure of the gas inside the body decreases, thus also reducing the opening pressure of the valve 7. On the other hand, a reduction of the volume of the cavity 9 will lead to an increase of the gas pressure inside the resilient body and thus an increase of the opening or "cracking" pressure of the valve 7. The volume of the cavity 9 may be varied by extending or retracting a movable end part 12 of the valve housing 8 with respect to a fixed part 13 of the valve housing 8. The two parts 12, 13 may each be threaded and may be screwed together.

In an alternative embodiment a valve 7 having a constant opening pressure is provided (FIG. 10). In this embodiment the valve housing 8 is formed by a tube having an inflow opening 10 at one end and being closed by a cap 14 at the opposite end. The cavity 9 is cylindrical. An outflow opening 11 is arranged in a sidewall of the tubular valve housing 8, approximately halfway between its two ends. In this embodiment the gas-filled resilient body 1 of FIG. 3 is used as valve member.

In another embodiment the lens-shaped or circular pillow-shaped body 1 of FIG. 5 is used as valve member in an overpressure valve 7, where the gas-filled resilient body 1 also functions as a buffer. In this embodiment the valve housing 8 has an inner part 13 and an outer part 12, and the gas-filled resilient body 1 is fixed with its sealed edge 4 between the two parts 12, 13 (FIG. 11). The inner part 13 has a curved wall 15 to which the body 1 conforms, while the outer part 12 has a valve seat 16 surrounding the outflow opening 11 which is engaged by the body 1. As long as a fluid pressure acting on the inflow opening 10 remains below a predetermined threshold value, it will merely serve to force the gas-filled resilient body 1 away from the curved wall 15 of the inner part 13 of the valve housing 8, so that the body 1 serves as a buffer. When the fluid pressure acting on the inflow opening 10 exceeds the threshold value, the gas-filled resilient body 1 is deformed by such an extent that the fluid is allowed to flow along the body 1 from the inflow opening 10 to the outflow opening 11. When a certain amount of fluid has escaped in this way, the fluid pressure acting on the inflow opening will fall below the threshold value, and the gas-filled resilient body 1 will return to its initial shape, closing off the outflow opening 11.

In another embodiment, the lens-shaped gas-filled resilient body 1 of FIG. 5 is again used as a valve member in a valve 7 having a two-part valve housing 8 (FIG. 12). In this embodiment the inflow opening 10 and outflow opening 11 are arranged next to each other in the inner part 13 of the valve housing 8. The outer part 12 is shaped as a cap. A space 17 between the cap 12 and the gas-filled resilient body 1 can be kept either at a predetermined pressure, or can be in fluid communication with the surroundings, so that ambient pressure acts on the body 1. This embodiment serves as a regular outlet valve, where the gas-filled resilient body 1 will be deformed when pressure acting on the inflow opening 10 exceeds the gas pressure in the body 1. As soon as the fluid pressure falls below the gas pressure, the resilient body 1 will resume its initial form and will again close off the inflow opening 10.

In yet another embodiment the gas-filled resilient body 1 serves as valve member in a pre-compression buffer valve 7 (FIG. 13). The valve 7 includes a tubular valve housing 8 that is closed by a wall 18 on one end and has an opening closable by a cap 14 at the opposite end. The cavity 9 accommodating the gas-filled resilient body 1 is cylindrical. Both an inflow opening 10 and an outflow opening 11 are arranged in sidewalls of the valve housing 8. In this embodiment, the inflow and outflow openings 10, 11 are arranged on opposite sides of the valve housing 8 and are offset in a longitudinal direction of the valve housing 8. A pump 19 is in fluid communication with the inflow opening 10 and provides fluid at pump pressure (FIG. 13B). As long as the fluid pressure that is delivered by the pump 19 is lower than the gas pressure inside the body 1, the valve 7 remains closed (FIG. 13A). When the fluid pressure exceeds the gas pressure, the body 1 will start to deform. In a first phase the deformation of the body 1 will simply create room in the cavity 9 for storing fluid under pressure. When the fluid pressure keeps increasing, the gas-filled resilient body 1 will eventually deform to such an extent that a flow path is established in the cavity 9 between the inflow opening 10 and the outflow opening 11 (FIG. 13B). This is the moment that the valve 7 opens.

In a further embodiment the gas-filled resilient body 1 is used as valve member in an outlet valve 7 that is arranged in an neck 20 of a container 21 (FIG. 14). In this embodiment the valve housing 8 is open at its bottom, which is in fluid communication with the inside of the container 21, while an outflow opening 11 is formed at its top, in fluid communication with the surroundings. In this embodiment it is the tubular gas-filled resilient body 1 of FIG. 3 that is used as the valve member. When the container 21, which has flexible walls, is squeezed the fluid pressure inside the container 21 will exceed the gas pressure inside the body 1. Consequently, the gas-filled resilient body 1 will be deformed and fluid will flow along the body 1 towards the outflow opening 11. When the flexible walls are no longer squeezed, the container 21 will resume its initial shape, thus drawing fluid back and reducing the fluid pressure inside the container 21. This pressure reduction will allow the gas-filled resilient body 1 to return to its original shape, thus closing off the flow path through the valve housing 7.

In a further embodiment the squeeze bottle of FIG. 14 may be provided with an adjustable pressure outlet valve 7 (FIG. 15). This adjustable pressure outlet valve 7 is constructed in similar way as the valve of FIGS. 8 and 9, i.e. it has a movable end part 12 which may be extended or retracted to increase or decrease the internal volume of the valve housing 8. When the internal volume is maximized (FIG. 15A), the gas-filled resilient body 1 may expand and its gas pressure may be reduced. Alternatively, when the internal volume is reduced by moving the end part 12 inward, the gas pressure inside the resilient body 1 is increased, thus increasing the opening pressure or "cracking pressure" of the valve 7. Like in the embodiment of FIGS. 8, 9, the end part 12 may be screwed into and out of the fixed part 13 of the valve housing 8.

Instead of creating a flow path by compression of the gas-filled resilient member 1, it is also conceivable that other types of deformation are used to allow the body 1 to act as a valve member in a valve 7. For instance, when use is made of a bent gas-filled resilient body 1 as valve member (FIG. 16), the valve 7 may open by further bending of the body 1. To that end the bent body 1 may be arranged in a two-part valve housing 8, in which a lower part 13 includes an inflow opening 10 and an upper part 12 includes an outflow opening 11. The upper part 12 defines a chamber 22 for clamping a part of the bent gas-filled resilient body 1 (FIG. 16A). Because the gas-filled resilient body 1, which is of the type shown in FIG. 1 or FIG. 3 will try to resume its initial state, the right hand part of this body 1 is pushed onto a valve seat 23 surrounding the inflow opening 10. When a fluid pressure acting on the inflow opening 10 is high enough, the gas-filled resilient body 1 will bend even further, thus moving away from the valve seat 23 and unblocking a flow path between the inflow and outflow openings 10, 11 (FIG. 16B). When the fluid pressure falls, the gas-filled resilient body 1 will return to its original position closing off the inflow opening 10.

In another embodiment a gas-filled resilient body 1 of the type shown in FIG. 3 is used as buffer in a pre-loadable metered dispenser or rapid-action dispenser 24 (FIG. 17). The rapid-action dispenser 24 comprises a chamber 25 filled with a fluid to be dispensed, and a piston 26 that is slidably received in the chamber 25. The piston 26 may be manually operable, e.g. by applying a force to an end face 27 thereof. The fluid filled chamber 25 surrounds a lower part of a buffer chamber 28 in which the gas-filled resilient body 1 is accommodated. In this embodiment the buffer chamber is tubular, and is closed at one end by a wall 29, while the other end is closed off by a cap 14 in which an outflow opening 11 is arranged. A valve body 30 is arranged in the outflow opening 11 and is movable between a position closing off the opening (FIG. 17A, B) and a position leaving free the opening (FIG. 17C). The valve body 30 may be fixed to the cap 14 by a frangible connection element (not shown). The valve body carries a hollow needle 31.

When the piston 26 is pressed towards the buffer housing 28 by exerting a force F on the end face 27, the fluid is forced from the chamber 25 through the inflow opening 10 into the buffer chamber 28 (FIG. 17B). As a result of the fluid pressure the gas-filled resilient body 1 will be compressed, so that the fluid pressure is stored in the gas buffer 1. In this situation the fluid is pressurized, but cannot yet be dispensed because the valve body 30 is still fixed in place, sealing the outflow opening 11. This is the stand-by situation. When the dispenser 24 is then placed with a tip of the hollow needle 31 against e.g. a skin of a subject to be treated, the frangible connection will break and the valve body 30 will be pushed out of the outflow opening 11. Consequently, pressurized fluid will flow from the interior of the buffer chamber 28 into the hollow needle 31, and from there to a location under the skin where the fluid is to be dispensed. This rapid-action dispenser 24 is especially suited for applications where the fluid has to be dispensed quickly and in a single shot, e.g. for administering a therapeutic substance.

In yet another embodiment the gas-filled resilient body 1 may be used as a buffer and overpressure valve in which overpressure is released by operation of a movable member 32 (FIG. 18). In this embodiment the valve 7 has a two-part valve housing 8 that is very similar to the valve housing of FIG. 14, but which further includes an operating member 32 which is movable in the outflow opening 11 to apply pressure on the gas-filled resilient body 1. In this embodiment, a fluid pressure exceeding the gas pressure in the body 1 and acting on the inflow opening 10 (FIG. 18B) will deform the body 1 so that it is lifted of the valve seat 23 and liquid is allowed into the space surrounding the gas-filled body 1. Then, when it has been determined that the pressure is too high, or if sufficient of the liquid to be dispensed has accumulated in the chamber 17, the operating member 32 can be moved downward through the outflow opening 11 to deform the gas-filled resilient body 1 and force it away from the upper valve seat 16. This allows the fluid to flow from the chamber 17 and exit the valve through the outflow opening 11 and a mouth 33 connected thereto (FIG. 18C).

In yet another embodiment the resilient body 1 is filled not just with gas, but also with a liquid or particulate material that is to be dispensed. In this embodiment the resilient body 1 acts as a pressurized container for use in a dispenser 34 (FIG. 19A, B). The dispenser 34 has a structure resembling that of the rapid-action dispenser of FIG. 17, in the sense that is includes a cylindrical housing 28 having a closed end wall 29 and an opposite end which is closed off by a cap 14. The cap 14 again has an outflow opening 11 which is closed off by a valve body 30 connected to the cap by a frangible connection element, and the valve body 30 carries a hollow needle 31. In this case the hollow needle has an end 35 which faces an upper end 3 of the gas-filled resilient body 1 and which serves as piercing member. Here again, when the hollow needle 31 is placed with its tip against e.g. a skin and then the dispensing device 1 is pushed further towards the skin, the needle 31 and the valve body 30 which it carries will be pushed inward, breaking the frangible connection and unblocking the outflow opening 11. At the same time, the sharp end 35 will pierce the top end 3 of the gas-filled resilient body. Then the contents of the body 1 will be emptied through the hollow needle 31 until the gas pressure inside the body 1 has fallen to a level equal to the ambient pressure.

In another embodiment of the dispenser 34 (FIG. 19C) the piercing member 35 is stationary and the gas-filled resilient body 1 can be pushed towards the piercing member in order to be pierced. In this embodiment the end wall 29 of the housing 28 is movable in the direction of the outflow opening 11 at the opposite end. The end wall 29 can be slidable or can be screwed into the housing 28. The gas-filled resilient body 1 can be introduced into the housing 28 after the end wall 29 has been removed. The gas-filled resilient body 1 then comes to rest on the piercing member 35. When the end wall 29 is replaced, the dispenser 34 is ready for use. By applying a force to the end wall 29, either by pushing or screwing it further into the housing 28, the gas-filled resilient body 1 is forcibly pushed onto the piercing member 35 and will be ruptured. Here again, the contents of the body 1 will be emptied through the hollow needle 31 until the gas pressure inside the body 1 has fallen to a level equal to the ambient pressure. In this embodiment the outflow opening 11 is provided with a spinner 57 to dispense the liquid in the form of a spray or mist 43. This embodiment can function as a single use atomizer, e.g. for personal care or for medicinal purposes.

An embodiment that is similar to that of FIGS. 19A and 19B is shown in FIG. 20, where the dispensing device 34 is intended for repeated use, rather than the one time use of the dispenser of FIG. 19.

In this embodiment the hollow needle 31 is fixedly arranged in a tubular element 36, which in turn is slidable in a sleeve 37. This sleeve 37 is threaded onto a threaded connector 38, which in turn can be screwed into a threaded open end of the housing 28. The slidable element 36 carrying the hollow needle 31 is biased to a position of rest away from the interior of the housing 28 by a compression spring 39 supported on the connector 38. In this embodiment the gas on the one hand and the liquid or particular material to be dispensed on the other, are shown to be separated. In order to avoid the gas escaping from the body 1, instead of the material to be dispensed, the dispensing device 34 has to be used in the illustrated orientation, i.e. with the hollow needle 31 oriented downward so that the gas will remain in the upper part of the resilient body 1.

The connector, sleeve, slidable element and needle of this embodiment could also be replaced by the valve mechanism of FIG. 18, if that valve were provided with a piercing member. In that way a dosed dispenser would be formed. If the outflow opening 11 were then provided with a spinner like the embodiment of FIG. 19C, a dosed sprayer would be obtained.

In yet another embodiment the resilient body 1 filled with gas and a liquid to be dispensed can form part of a precision applicator 51 (FIG. 21). An applicator housing 52 can be connected to one end 3 of the resilient body 1. In the illustrated embodiment the applicator housing 52 tapers from a broad basis 53 which accommodates the end 3 of the resilient body 1 to a narrow outflow opening 11. A tipped valve 54 closes off the outflow opening 11. The valve 54 is biased towards its closed position by a spring 55. The applicator 51 further has a cutting or piercing member (not shown) with which an opening is formed in the resilient body 1 to allow the gas to press the liquid into the conical applicator housing 52. To apply the liquid to a surface, the applicator 51 is moved towards the surface so as to bring the tipped valve 54 in contact with the surface. The tipped valve 54 will then be pushed into the applicator housing 52 against the biasing force of the spring 55, thus freeing the outflow opening 11 so that a small amount (drop) of liquid can be applied to the surface (FIG. 21B).

In order to obtain a predetermined spring characteristic, use may be made of a gas-filled resilient body 1 having a plurality of chambers 47 (FIG. 22). In this embodiment each chamber has a pillow shape like the gas-filled resilient body 1 that is illustrated in FIG. 4. These pillow-shaped chambers are in fluid communication through ports 46, and only the two outermost chambers 47 are sealed at their outward facing ends by welds 4. The ports 46 are arranged at hinge lines 48 which allow the chambers 47 to be folded together to form a stack (FIG. 22B). Since the chambers 47 are connected by single hinges 48, they are not mutually parallel, but enclose an angle when they are stacked. When the resulting stack is then subject to a compression force F, the folded chambers 47 of the gas-filled resilient body 1 form a spring 40 having a predetermined spring characteristic. The spring characteristic can be adjusted by varying the number of chambers 47 in the stack, the internal gas pressure and/or the resiliency of the material from which the gas-filled resilient body 1 is made.

The spring may be arranged in a two-part spring housing including a fixed part 41 and a movable part 42 (FIG. 23). Both the fixed part 41 and the movable part 42 include a central opening 44, 45 to allow air to escape when the spring is compressed (FIG. 23B) and to enter when the spring is released (FIG. 23A).

Instead of using the internal gas pressure and the resiliency of the body 1 to withstand compression forces, it is also conceivable to make use of the resistance to bending which the gas-filled resilient body 1 will have to form a spring 40 (FIG. 24). When one end 3 of the gas-filled resilient body 1 is fixed, in this case for instance the lower end 3, then the opposite free end 3 may be subject to a bending force F (FIG. 24A), which will be reacted by a reaction force $F_R$ resulting from the internal gas pressure and the inherent resiliency of the material of the body 1 (FIG. 24B). This configuration again results in a spring 40 having a different spring characteristic than the springs 40 of the previous embodiments.

Such a spring 40 can be used e.g. as a return spring for biasing a trigger 50 of a trigger sprayer mechanism 56 including a nozzle 58 toward its position of rest (FIG. 25A) after the trigger 50 has been pulled to operate the trigger sprayer 56 (FIG. 25B). Here, the lower end 3 of the gas-filled resilient body is fixed in a support 57 that is attached to the front of the trigger sprayer mechanism 56. Obviously, this is merely one example of the way in which such a bent spring can be used.

In order to avoid uncontrolled deformation of a gas-filled resilient body 1 when it is subjected to bending forces, the body 1 may be attached to or supported by a curved support element 49 to form a C-spring 40 (FIG. 26). This C-spring 40 is shown both in its position of rest and in its further deflected position when subjected to a load (indicated by primed reference numerals).

As described above, the invention allows gas-filled resilient bodies to be used for a variety of purposes. Although a great number of exemplary embodiments have been described, further variations and modifications are conceivable. The scope of the invention is defined solely by the following claims.

The invention claimed is:

1. A method of using a partially gas-filled resilient body, comprising:
    using the partially gas-filled resilient body as a gas-propelled dispenser,
    wherein the resilient body is filled with gas and a material to be dispensed; and
    wherein the material is dispensed by piercing the resilient body.

2. The method of claim 1, wherein the material to be dispensed is a liquid or a particulate material.

3. A rapid-action dispensing device, comprising:
    means for pressurizing a liquid to be dispensed,
    an outlet opening closed off by a manually operable valve, and
    a resilient body filled with gas only arranged in a buffer housing between the pressurizing means and the outlet so as to buffer the pressurized liquid in a volume defined between the gas-filled resilient body and a wall of the buffer housing by compressing the gas-filled resilient body until the valve is manually opened.

4. A dispensing device, comprising:
    a housing having an outlet opening,
    a resilient body partially filled with gas and partially filled with a material to be dispensed, and
    a piercing member for piercing the resilient body so as to allow the material to be urged out by the gas,
    wherein the piercing member and the resilient body are movable with respect to each other.

5. The dispensing device of claim 4, wherein the piercing member is tubular and extends through the outlet opening.

6. The method of claim 1, wherein the resilient body is pierced by moving the resilient body and a piercing member with respect to each other.

7. The method of claim 6, wherein one of:
    the resilient body is held stationary and the piercing member is moved; or
    the piercing member is held stationary and the resilient body is moved.

8. The method of claim 6, wherein the piercing member comprises a hollow needle through which the material is dispensed.

9. The method of claim 1, wherein the material is urged out of the resilient body by the gas, and wherein the material is dispensed until a pressure of the gas is equal to ambient pressure.

10. The rapid-action dispensing device of claim 3, wherein the pressurizing means comprise a piston that is slidably received in a chamber filled with the liquid to be dispensed, said chamber being in fluid communication with the buffer housing through an inflow opening.

11. The rapid-action dispensing device of claim 3, wherein the outlet opening is arranged in a cap closing off the buffer housing, and wherein the valve includes a valve body arranged in the outlet opening and movable between a position closing off the opening and a position leaving free the opening.

12. The rapid-action dispensing device of claim 11, wherein the valve body is fixed to the cap by a frangible connection element.

13. The rapid-action dispensing device of claim 11, wherein the valve body carries a hollow needle.

14. The dispensing device of claim 4, wherein the resilient body is arranged stationary in the housing and the piercing member is inwardly movable with respect to the housing.

15. The dispensing device of claim 14, wherein the outlet opening is arranged in a cap closing off the housing, and wherein the outlet opening is closed off by a valve body connected to the cap by a frangible connection element.

16. The dispensing device of claim 15, wherein the piercing member comprises a hollow needle carried by the valve body.

17. The dispensing device of claim 4, wherein the piercing member is stationary and the resilient body is movable in the housing towards the piercing member.

18. The dispensing device of claim 17, wherein an end wall of the housing is movable in the direction of the outlet opening at an opposite end of the housing.

19. The dispensing device of claim 14, wherein the piercing member comprises a hollow needle fixedly arranged in an element which is slidable in the housing, the slidable element being biased to a position of rest away from an interior of the housing by a spring.

20. The dispensing device of claim 4, wherein the housing is an applicator housing connected to one end of the resilient body, the applicator housing tapering from a base which accommodates the end of the resilient body to the outlet opening, wherein a tipped valve biased by a spring closes off the outlet opening.

* * * * *